(12) United States Patent  (10) Patent No.: US 7,474,965 B2
Johnson et al.  (45) Date of Patent: Jan. 6, 2009

(54) SYSTEM AND METHOD FOR IDENTIFYING MOLECULES

(75) Inventors: Bradley Johnson, Berkeley, CA (US); Rehan M. Khan, Berkeley, CA (US); Noam Sobel, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/099,326

(22) Filed: Apr. 5, 2005

(65) Prior Publication Data

US 2006/0224332 A1  Oct. 5, 2006

(51) Int. Cl.
*G06F 19/00* (2006.01)
(52) U.S. Cl. .............. 702/22; 702/24; 702/27; 73/25.04; 73/29.01; 73/23.27
(58) Field of Classification Search .......... 702/22, 702/24, 27; 73/23.02, 53.01, 30.01, 61.44, 73/25.4, 29.01, 23.27; 700/265, 266
See application file for complete search history.

(56) References Cited

U.S. PATENT DOCUMENTS

| 4,953,407 | A | * | 9/1990 | Malaczynski et al. | ..... 73/861.09 |
| 5,459,998 | A | * | 10/1995 | Hosoya et al. | ................ 60/284 |
| 6,049,380 | A | * | 4/2000 | Goodwin et al. | ............ 356/317 |
| 6,076,392 | A | * | 6/2000 | Drzewiecki | ................. 73/23.2 |
| 6,309,886 | B1 | * | 10/2001 | Ambrose et al. | ............... 436/63 |
| 6,495,892 | B2 | * | 12/2002 | Goodman et al. | ........... 257/414 |
| 6,746,960 | B2 | * | 6/2004 | Goodman | ................... 438/689 |

* cited by examiner

*Primary Examiner*—Tung S Lau
*Assistant Examiner*—Hien X Vo
(74) *Attorney, Agent, or Firm*—Brian N. Young; Trellis IP Law Group, PC

(57) ABSTRACT

A system and method for identifying molecules. Molecules are identified from a gaseous matter having the molecules and flowing at two different flow rates. A system and method for identifying a substance. A particle which is indicative of a substance is identified from matter having the particle and flowing at two different flow rates. After the particle is identified, the substance is identified.

21 Claims, 20 Drawing Sheets

Mass Flow Controllers

SYSTEM AND METHOD FOR IDENTIFYING MOLECULES

FIELD OF THE INVENTION

Embodiments of the present invention generally broadly relate to identifying minuscule or minute matter. More specifically, embodiments of the present invention generally provide for a system and method for identifying molecules, such as molecules which furnish an odor. Additionally, embodiments of the present invention relate to the preparation and delivery of molecules to a sensing device for identification of the molecules.

BACKGROUND OF THE INVENTION

Dogs are used for detecting and determining the nature of substances. For example, sniffing dogs are used to detect contraband ranging from fruit, to currency, to drugs and bombs. Sniffing dogs are also used for medical diagnosis purposes, such as for detecting melanoma, bladder cancer, and the onset of epileptic seizures. However, dogs are susceptible to making mistakes, are costly and time consuming to train and maintain, may harbor human communicable diseases, and present other sanitary, safety, and practical problems. Therefore, what is needed and what has been invented is a system and method for identifying a substance, particularly the molecules of a substance.

SUMMARY OF EMBODIMENTS OF THE INVENTION

Embodiments of the present invention provide a method for identifying molecules. The method comprises flowing at a first flow rate a gaseous matter having molecules, flowing at a second flow rate the gaseous matter having the molecules, and identifying the molecules.

Embodiments of the present invention also provide a method for identifying a substance. The method comprises flowing at a first flow rate matter having at least one particle indicative of a substance, flowing at a second flow rate the matter having at least one particle, identifying the particle, and identifying the substance from the identified particle.

Embodiments of the present invention provide an apparatus for identifying molecules comprising a preparation assembly for preparing a medium for admixing with molecules, a mixing assembly for mixing molecules with the prepared medium, and an identifying assembly for identifying the molecules.

Embodiments of the present invention further also provide a computer-readable medium including instructions executable by a computer comprising one or more instructions for setting a first flow rate of a gaseous matter having molecules, one or more instructions for setting a second flow rate of the gaseous matter having the molecules, and one or more instructions for identifying the molecules.

These provisions together with the various ancillary provisions and features which will become apparent to those skilled in the art as the following description proceeds are attained by the systems and methods of the present invention, preferred embodiments thereof being shown with reference to the accompanying drawings, by way of example only, wherein:

DETAILED DESCRIPTION OF PREFERRED EMBODIMENTS OF THE INVENTION

Figure 1:
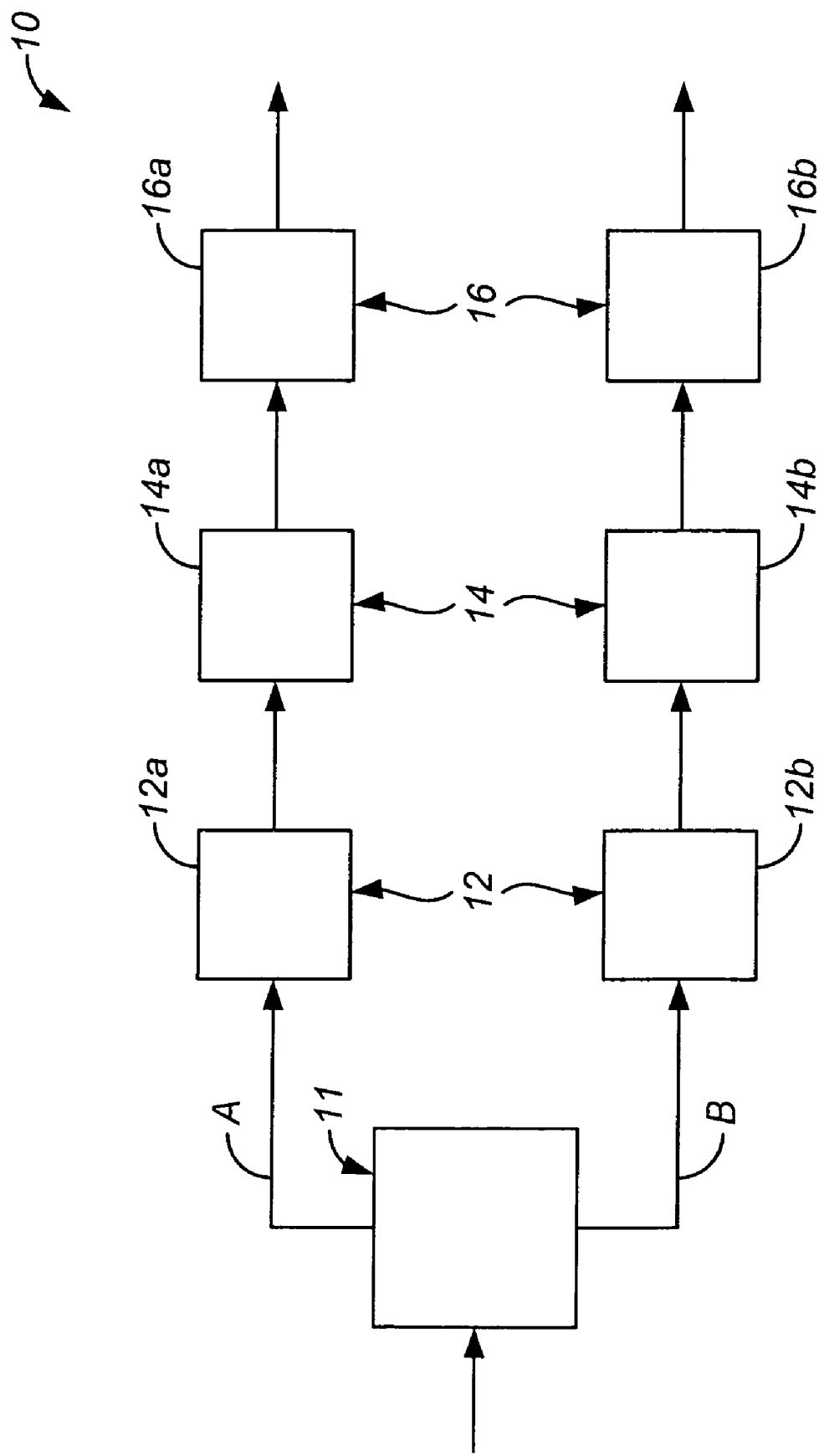
FIG. 1 is a schematic flow diagram exemplifying a system for identifying minuscule or minute matter of any suitable substance in accordance with embodiments of the invention.

Referring in detail now to the drawings wherein similar parts of embodiments of the present invention are identified by like reference numbers, there is seen in FIG. 1 a schematic flow diagram exemplifying a system, generally illustrated as 10, for identifying minuscule or minute matter of any suitable substance, in accordance with various embodiments of the present invention. The minuscule or minute matter to be identified may be any suitable minuscule or minute matter, such as one or more molecules, particulate material having any suitable dimension(s), etc. For purposes of illustrating embodiments of the present invention, the minuscule or minute matter is a molecule, particularly molecules furnishing an odor (e.g., odorant molecules). As known to those in the art, a molecule represents a stable configuration of atomic nuclei and electrons bound together by electrostatic and electromagnetic forces. A molecule includes the smallest particle of any substance, representing the simplest structural unit that displays and possesses the characteristic physical and chemical properties and qualities of that substance. While embodiments of the present invention will by illustrated with one or more molecules as being the minuscule or minute matter to be identified, it is to be understood that such illustration is for exemplary purposes only and is not to unduly limit the scope of the present invention. The spirit and scope of the present invention includes the minuscule or minute matter to be identified as being any suitable minuscule or minute matter. It is to be understood that odor is a perceptual phenomena, not a unique attribute of a molecule or mixture of molecules. The same molecule may provide a different odor to different people, and two different molecules may furnish the same odor. Some molecules are odorless. Thus, by identifying the molecules, the substance may be identified without regard to odor. However, a generalized determination of odor may be provided or extrapolated from the identified substance, particularly for those substances that have a distinct odor which does not generally vary.

As illustrated in FIG. 1 the system 10 includes a reservoir 11 for receiving and/or storing a medium for transporting and/or carrying one or more molecules (i.e., the minuscule or minute matter) of a substance. The system 10 also includes a preparation assembly, generally illustrated as 12, a mixing assembly, generally illustrated as 14, and an identifying assembly, generally illustrated as 16. The preparation assembly 12 prepares the medium for the mixing assembly 14 where the molecules are admixed with the prepared medium. The identifying assembly 16 identifies the molecules that are contained in the prepared medium.

For various embodiments of the present invention, medium in reservoir 11 of FIG. 1 may be divided into stream A and stream B. The flow rates of the medium in stream A and stream B are preferably different. The medium of stream A passes into preparation assembly 12a where the medium is prepared for being admixed with molecules in mixing assembly 14a. After molecules have been added to and/or admixed with the prepared medium of stream A, the admixture of prepared medium and molecules is then passed into the identifying assembly 16a where the molecules that are contained in the prepared medium are identified. From identifying assembly 16a, the admixture of prepared medium and molecules may be transported to any desired location, or discarded through an exhaust.

The medium of stream B may be processed similarly to the manner in which medium of stream A is processed. More particularly, the medium of stream B passes into preparation assembly 12b where the medium is prepared for being admixed with molecules in mixing assembly 14b. After molecules have been added to and/or admixed with the prepared medium of stream B, the admixture of prepared medium and molecules is then passed into the identifying assembly 16b where the molecules that are contained in the prepared medium are identified. From identifying assembly 16b, the admixture of prepared medium and molecules may be transported to any desired location, or discarded through an exhaust. The identification of the molecules in the prepared medium of streams A and B may be for any suitable purposes. For various embodiments of the present invention the molecules are identified for determining odor of a substance, more particularly for determining the substance containing and/or producing the identified molecules.

The medium may be any suitable medium that is capable of transporting and/or carrying molecules of a substance for identification purposes. By way of example only, the medium for the various embodiments of the present invention may include a liquid and/or a gas. If the medium comprises a liquid, the liquid may be any suitable liquid that is capable of admixing with or carrying the molecules for identification purposes in accordance with various embodiments of the invention. A suitable liquid may be an aqueous liquid, such as water (e.g., distilled water). If the medium comprises a gas, the gas may comprise any suitable gas that is capable of transporting and/or carrying the molecules. Preferably, the gas comprises an odorless gas. More preferably, the gas comprises a colorless, odorless, tasteless gas, or gaseous mixture, such as air (e.g., medical grade air) having nitrogen, oxygen, argon, carbon dioxide, neon, helium, and other gases. When the gas for transporting and/or carrying the molecule(s) is air, the molecule(s) is/are admixed with the air, such as to be air-borne and disseminated diffusively throughout the air.

For purposes of illustrating embodiments of the present invention, the medium for transporting and/or carrying one or more molecules comprises air (e.g., medical grade air). While embodiments of the present invention will by illustrated with air as being the suitable medium for transporting and/or carrying one or more molecules to be identified, it is to be understood that such illustration is for exemplary purposes only and is not to unduly limit the scope of the present invention. The spirit and scope of the present invention includes any suitable medium for transporting and/or carrying one or more molecules for admixing with and/or carrying the molecules, such as liquids or a mixture of liquids and a gas (e.g., air).

While FIG. 1 only illustrates two streams (i.e., streams A and B) of medium, preferably at two different flow rates, it is to be understood that the spirit and scope of the present invention includes the employment of any number of streams of medium flowing at various flow rates, at least some or all of which may be different from each other. Preferably, all streams of medium have a different flow rate with respect to each other. For embodiments of the present invention, the flow rate of the medium of the streams may be selected from the following flow rates, with each stream having a different flow rate: about 6 LPM (liters per minute), about 9 LPM, about 12 LPM, and about 15 LPM. Thus, if two streams are employed and one stream has a flow rate of about 6 LPM, the other stream would have a flow rate selected from the remaining flow rates (e.g., about 9 LPM or about 12 LPM or about 15 LPM).

Figure 2:
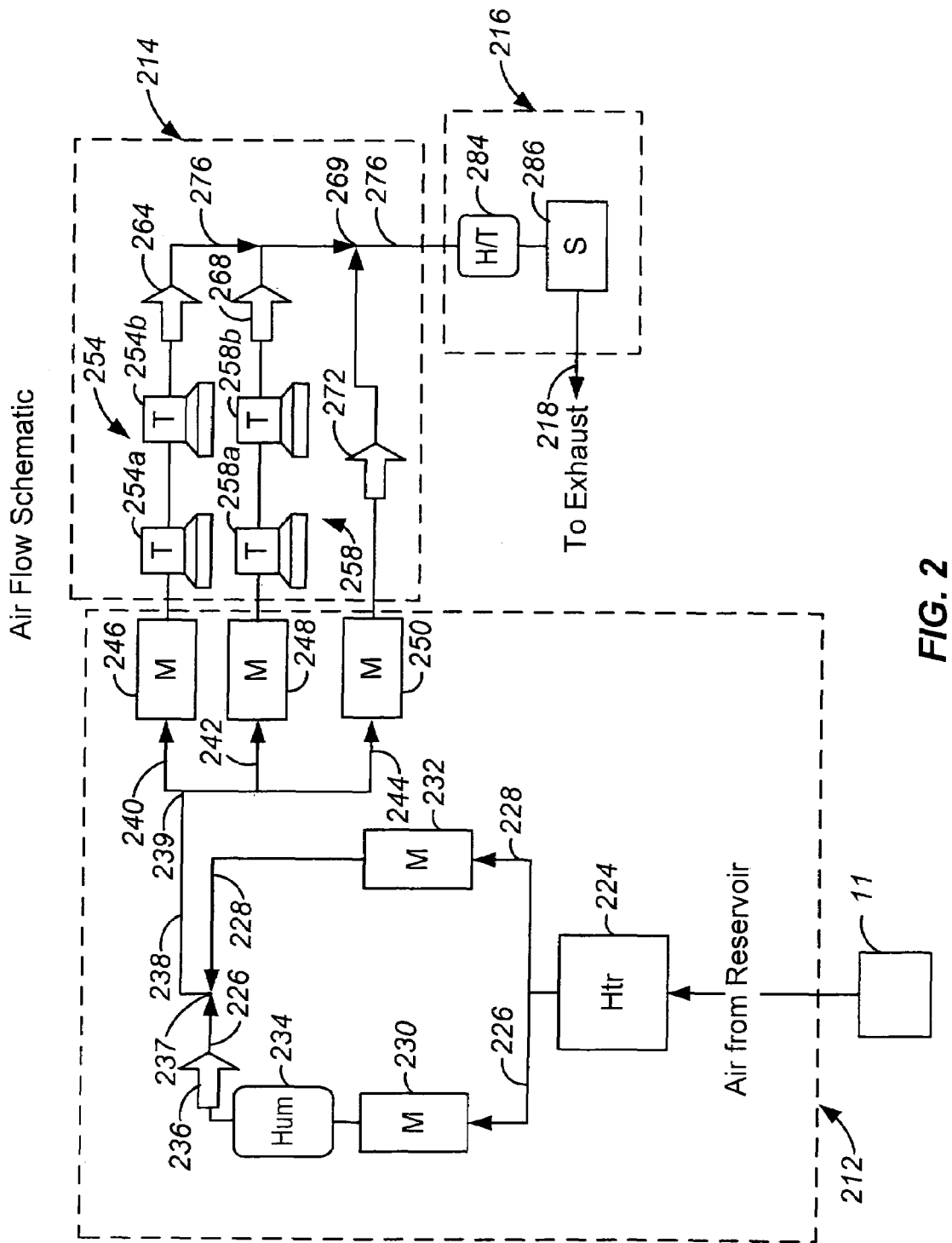
FIG. 2 is a schematic air (i.e., medium) flow diagram for preparing the air to be mixed with molecules (i.e., minuscule or minute matter), for mixing the prepared air with the molecules, and for identifying the molecules in the prepared air.

Referring now to FIG. 2, there is seen a schematic flow diagram for preparing air (i.e., medium) to produce prepared air, for mixing the prepared air with molecules (i.e., minuscule or minute matter), and for identifying the molecules in the prepared air. Air from a tank or reservoir (e.g., reservoir 11) passes into preparation assembly 212 where the air is prepared for being admixed with molecules in mixing assembly 214. After molecules have been added to and/or admixed with the prepared air in the mixing assembly 214, the admixture of prepared air and molecules is then passed into the identifying assembly 216 where the molecules that are contained in the prepared air are identified. From identifying assembly 216, the admixture of prepared air and molecules may be transported to any desired location, or discarded via line 218 through an exhaust.

In an embodiment of the present invention, the preparation assembly 212 includes a heater 224 which receives air from the reservoir 11. Air passes into the heater 224 where the air is heated to ambient room temperature. Due to temperature changes when a gas expands, air from a compressed source (e.g., from reservoir 11) is much colder than room temperature and heating is necessary to eliminate temperature effects to the sensor (identified as 286 below). Additionally room temperature should be controlled as much as practical. Heater 224 may be any suitable heater, such as an Osram-Sylvania Threaded Inline Air Heater (Danvers, Mass., www.sylvania.com). A temperature controller, such as an OMRON (Omron Corporation, Shiokoji Horikawa, Shimogyo-ku, Kyoto, 600-8530 Japan, www.omron.com) temperature controller, modulates the heater 224 to match the air temperature against the set point temperature.

Referring now to FIG. 17, there is seen a schematic diagram of an embodiment of a heating subsystem, generally illustrated as 1700 and including a temperature controller 1710, a temperature probe 1720, a relay 1730, and a power supply 1740. The temperature controller 1710 has an LED display and several buttons for visual feedback and user manipulation of the temperature controller 1710 which also includes connections for being coupled to the temperature measuring probe 1720 that comes in contact with the air for measuring the temperature of same. The temperature controller 1710 also has an output that is suitable for control of the electromechanical relay 1730, such as a Tyco/B&S T73S5D15-12. The relay 1730 closes its contact to allow current to pass through a pair of terminal conductors 1732 and 1734. This contact is closed when a sufficient control voltage (e.g., 12 Vdc) relay is applied to the terminal pair of conductors 1736 and 1738. The contact is open when the voltage is too low or absent. The actuating of the relay 1730 connects the power supply 1740 to the heater 224 for effectively warming air entering the heater 224. The temperature controller 1710 contains software that implements an auto-tuning PID loop. It is auto-tuning in the regard that the user need not choose values for the P, I, and D control factors. The software modulates relay 1730 in an effort so temperature input from the temperature probe 1720 matches the user-defined temperature set point.

The measurement of air temperature by the temperature probe 1720 for feedback in the heating process can be from any suitable temperature transducer, such as a Newport Electronics, Inc. Precision Fine Wire Thermocouple, Type J (Santa Ana, Calif., www.newportinc.com) that provides input to the temperature controller 1710. The temperature controller 1710, such as the OMRON, implements a software PID control loop in which the temperature input from the temperature probe 1720 is compared against the user-defined input and the controller 1710 modulates the heater 224 accordingly. If the temperature of the molecules/warm/humidified air at the temperature sensor (identified as 284 below) is too low, the temperature controller 1710 actuates relay 1730 which in turn applies power to heater 224 to increase the temperature of the air leaving heater 224. Similarly, if the temperature of the air at the temperature sensor (identified as 284 below) is too high, the temperature controller 1710 turns relay 1730 off so that the heater 224 is turned off and the temperature of the air leaving heater 224 decreases. The temperature of the air at the temperature sensor (identified as 284 below) is preferably ambient (room) temperature.

After the air is heated by heater 224, it is divided and passed into conduits 226 and 228 which respectively include or contain mass-flow controllers 230 and 232, which may regulate and/or control the flow of air. From mass-flow controller 230 in conduit 226, air is humidified by suitable humidifier 234 and passes through one way valve 236. The humidity of the warm air passing out of the humidifier 234 may be any suitable humidity, preferably a humidity matched to the ambient humidity (room humidity) in proximity to the humidity sensor (identified as 286 below). Humidification of the air may be conducted by any suitable humidifier, such as humidifier 234*a* in FIG. 4. As further explained below, the humidity sensor (identified as "284" below) monitors the humidity of the molecules/warm/humidified air such that if the humidity of the molecules/warm/humidified air at the humidity sensor is not at a desired humidity (e.g., ambient humidity), a signal may be transmitted to mass flow controllers 230 and 232 to humidifier 234 to accordingly adjusts (i.e., decrease or increase) the ratio of air humidity of the warm/humidified air leaving humidifier 234 such that when the molecules/warm/humidified air arrives at the humidity sensor, it will have the desired humidity.

As illustrated in FIG. 4 humidifier 234*a* may comprise a bubbler type humidifier having a canister 410 containing a humidifier liquid 412 (e.g., distilled water). A conduit head 414 is supported by the canister 410 and has concentrically disposed with respect thereto conduit 416 for conducting and/or conveying air into the liquid 412. Humidified air bubbles through and leaves the liquid 412, passes through the annulus 418, and exits the annulus 418 through exit conduit 420.

Air in conduit 228 passing into and through mass-flow controller 232 is relatively dry air vis-à-vis the humidified air exiting humidifier 234 and passing through one way valve 236. From controller 232 the dry air passing through conduit 228 is commingled with and/or admixed at juncture 237 with the humidified air passing through conduit 226 and one way valve 236. The ratio of warm/humidified air to warm dry air allows for adjustment of humidity. The ratio by weight of warm/humidified air to warm dry air may be any suitable ratio, preferably a ratio such that the ratio is not skewed to one side as to prevent the mass-flow-controllers adequately dynamic range. The flow controllers 230 and 232 have minimum and maximum flow rates and if the ratio is weighted towards one mass-flow-controller (say for example 90% wet-air and 10% dry-air) then there is not much room for further adjustments should for example the water-level in the humidifier 234 decrease sufficient to cause the output humidity to decrease. For various embodiments of the invention, the ratio by weight mass of warm/humidified air to warm dry air ranges from about 30.0% to about 70.0%.

Humidity is regulated by software code that implements a feedback loop to adjust the ratio of warm/humidified air to warm air based on measured humidity. A humidity sensor (identified as 284 below) disposed in proximity to a sensor assembly (identified as 286 below) and providing feedback for a software PID loop that regulates the humidity of the warm/humidified air leaving the humidifier 234. If the humidity of the molecules/warm/humidified air at the humidity sensor (identified as 284 below) is too low, a signal is sent to controllers 230 and 232 so that more wet air enters junction 237 via controller 230 and controller 232 reduces the mass dry air by the same amount. Similarly, if the humidity of the molecules/warm/humidified air at the humidity sensor (identified as 284 below) is too high, a signal is sent to controllers 230 and 232 so that more dry air enters junction 237 via controller 232 and controller 230 reduces the mass of wet air by the same amount.

PID stands for Proportional-Integral-Derivative, a type of feedback controller whose output, a control variable (CV), is generally based on the error (e) between some user-defined set point (SP) and some measured process variable (PV). Each element of the PID controller refers to a particular action taken on the error. Proportional means error multiplied by a gain, $K_p$. This is an adjustable amplifier. In embodiments of the present invention $K_p$ is responsible for process stability: too low and the PV can drift away; too high and the PV can oscillate. Integral means the integral of error multiplied by a gain, $K_i$. In embodiments of the present invention $K_i$ is responsible for driving error to zero, but to set $K_i$ too high is to invite oscillation or instability or integrator windup or actuator saturation. Derivative means the rate of change of error multiplied by a gain, $K_d$. In embodiments of the present invention, $K_d$ is responsible for system response: too high and the PV will oscillate; too low and the PV will respond sluggishly. The designer or user of embodiments of the invention should also note that derivative action amplifies any noise in the error signal.

Juncture 237 is the juncture point of conduits 226 and 228 with conduit 238 which terminates at juncture 239. Warm and humidified air flowing through conduit 238 splits or divides at juncture 239 for flowing through conduits 240, 242 and 244 for respectively delivering warm and humidified air to mass-flow controllers 246, 248, and 250, which is part of the mixing assembly 214 where molecules are admixed with the prepared air. In addition to controllers 246, 248, and 250, mixing assembly 214 includes sub-mixing assemblies 254 and 258, and one way valves 264, 268, and 272.

Sub-mixing assembly 254 has mixers 254a and 254b for mixing and/or commingling molecules with warm and humidified air flowing from controller 246. A mixture of molecules and warm/humidified air leaves mixer 254b and passes through one-way valve 264 and into conduit 276. Sub-mixing assembly 258 has mixers 258a and 258b for mixing and/or commingling molecules with warm and humidified air flowing from controller 248. A mixture of molecules and warm/humidified air leaves mixer 258b and passes through one way valve 268 and into conduit 276. Warm/humidified air passing through and/or from controller 250 passes directly to and through one way valve 272 (without passing through any sub-mixer or sub-mixing assembly) for subsequently mixing at juncture 269 with the mixtures of molecules and warm/humidified air leaving the one way valves 264 and 268 and passing into conduit 276. The pressure and flow rate of warm/humidified air through and from controllers 246, 248, and 250 (and from one way valves 264, 268, and 272) may be the same, different, or may vary accordingly.

The concentration of molecules in the mixture of molecules/warm/humidified air prepared by sub-mixing assemblies 254 and 258 may be any suitable concentration. The concentration is dependent on the actual substance in the mixing vessels (i.e., mixers 254a, 254b, 258a, and 258b) vis-à-vis vapor pressure. The concentration of molecules at junction 269 is related to the saturated vapor concentration of the molecules, and preferably depends on the sensitivity of sensor (identified as "286" below). The concentration should be as high, or higher, than the minimum quantity detectable by the chosen sensor (e.g. threshold concentration). The concentration should be as low, or lower, than the maximum quantity detectable by the chosen sensor (e.g. saturation concentration).

The sub-mixing assemblies 254 and 258 may be any suitable mixing assemblies which are capable of producing and/or mixing molecules with warm and humidified air. By way of example only, each sub-mixing assemblies 254 and 258 may comprise a molecule canister (e.g., a thimble) containing a substance which is to be identified. For various embodiments of the present invention, the molecule canister comprises a ¾" stainless steel street-tee with a ¾" hex cap filled with liquid (e.g., from about 1 ml to about 3 ml of the substance, such as 2 ml of the substance). Parts for the molecule canisters may be purchased commercially Duhig and Co., Inc., www.duhig.com. As the molecules evaporate from the liquid molecule, the molecules admix with the warm/humidified air supplied by controllers 246 and 248. Having two or more molecule canisters in each of the sub-mixing assemblies allows higher volumetric flow rates of air to be saturated. Having two or more controllers (i.e., controllers 246 and 248 in each of the sub-mixing assemblies (i.e., sub-mixing assemblies 254 and 258) allows creation of binary molecule mixtures. A binary molecular mixture is one that contains two molecular species at the same or different concentrations in the warmed/humidified air stream. Having a flow-controller for each molecular source allows the concentration of each species to be controlled independently. For example, if only one flow-controller was used and two liquids of differing compositions were loaded into the same sub-mixing assembly then the same amount of air would flow over each species. It would not be possible to increase the concentration of one species and decrease the concentration of the other.

The warm and humidified air flowing from controller 250 and passing through one way valve 272 is commingled with and/or admixed at juncture 269 with the mixture of molecules/warm/humidified air prepared by sub-mixing assemblies 254 and 258, leaving one way valves 264 and 268, and flowing through conduit 276. The ratio of molecules/warm/humidified air to warm/humidified air allows for adjustment of the concentration of the molecules in the molecules/warm/humidified air. Stated alternatively, warm/humidified air from controller 250 and passing through one way valve 272 provides pure air and dilutes the odorized air (i.e., the molecules/warm/humidified air) to modulate, regulate, and control molecular concentration (i.e., the concentration of the molecules). It should be understood that controller 250 does not necessarily have to allow any warm and humidified air to pass through it. If the concentration of the molecules in the molecules/warm/humidified air is suitable, no dilution with warm/humidified air from controller 250 would be required.

After the mixture of prepared molecules/warm/humidified air (which may or may not have been diluted with warm/humidified air from controller 250) passes juncture 269, it continues to flow through conduit 276 for subsequent passing into the identifying assembly 216 for identifying the molecules that are contained in the prepared molecules/warm/humidified air. The identifying assembly 216 comprises a humidity and temperature sensor 284 disposed in proximity to a sensor assembly 286.

The prepared molecules/warm/humidified air flows by the humidity and temperature sensor 284 for detecting the humidity and temperature of the prepared molecules/warm/humidified air. As previously indicated, the humidity and temperature sensor 284 monitors the humidity and temperature of the molecules/warm/humidified air such that if the humidity and/or temperature of the molecules/warm/humidified air at the humidity and temperature sensor 284 is not at a desired humidity (e.g., ambient humidity) and/or temperature (e.g., ambient temperature), a signal may be transmitted to humidifier 234 and/or to heater 224 to accordingly adjusts (i.e., decrease or increase) the humidity of the warm/humidified air leaving humidifier 234 and/or temperature of the warm air leaving the heater 224, such that when the molecules/warm/humidified air arrives at the humidity and temperature sensor 286, it will have the desired humidity and temperature (e.g., ambient humidity and temperature).

After the prepared molecules/warm/humidified air flows by the humidity and temperature sensor 284, it is then directed to the sensor assembly 286 where the molecules (i.e., the substance molecules) are identified. As the molecules pass the sensor assembly 286 an immeasurable proportion associate with the sensor assembly 286 and illicit changes in one or more of the sensor's properties (e.g. volume, electrical conductivity, etc). This transduction of molecule to sensor property creates a signature for that particular molecule. From the created signature, the molecule may be identified by matching the created signature with a molecular signature associated with that molecule and previously determined and stored in a data bank. A description of the sensor assembly 286 will be presented hereafter by referencing the drawings, particularly FIGS. 5 and 6.

For embodiments of the present invention, it is to be understood that the FIG. 2 schematic flow diagram for delivering molecules to the sensor assembly 286 may represent one of the two (i.e., two or more) flow streams (i.e., streams A or B) of the procedure illustrated in FIG. 1. The other flow stream of the two flow streams of the procedure illustrated in FIG. 1 may also be conducted in accordance with the FIG. 2 schematic flow diagram. The collecting of sample data (e.g., with the sensor assembly 216) from the two flow streams is preferably performed simultaneously while the two flow streams are flowing at different flow rates. It is also to be understood that streams A and B could be the same physical device, with stream A being conducted at one flow rate through the device followed by stream B subsequently flowing at a different flow rate through the same device. Additional streams may follow after A and B. In practice, such a redundant use of hardware reduces physical size requirements of a device but increases operation time.

As previously indicated, the humidity and temperature sensor 284 regulates humidity of the air leaving the mass-flow controller 230 and flowing into the humidifier 234 by providing feedback for a software PID loop (e.g., software associated with a computer assembly such as that in FIG. 3) that regulates the ratio of humidified air from humidifier 234 to the warm air flowing from controller 232. If the humidity and temperature sensor 284 detects that the prepared molecules/warm/humidified air has insufficient or too much humidity, a signal (i.e., feedback) from a software PID loop is transmitted to the flow controllers 230 and 232 to adjust the ratio of day and wet air when mixed together at juncture 237. Similarly, if the humidity and temperature sensor 284 detects that the prepared molecules/warm/humidified air has too low or too high of a temperature, a signal (i.e., feedback) from hardware temperature controller 1710 is transmitted to the heater 224 to either increase or decrease the temperature of the warm air leaving the heater 224.

The flow rate of the pneumatic matter (e.g., warm/humidified air and/or molecules/warm/humidified air) through the preparation assembly 212, through the mixing assembly 214, and through the identifying assembly 216 may be any suitable flow rate.

The pressure of the pneumatic matter flowing through the preparation assembly 212, through the mixing assembly 214, and through the identifying assembly 216 may be any suitable pressure to allow the desired flow range. Minimum pressure requirements depend on the length and diameter of the conduits. Furthermore, the mass-flow-controllers have minimum pressure requirements or they will afford a small leak when no flow is sought. It is important that the pressure drop across each controller is sufficient to prevent leakage. For the controllers specified, they are typically shipped with a minimum pressure requirement of about 20 PSI. This results in a pressure at reservoir 11 of about 30 to about 40 PSI. If the conduits are narrow and long, more pressure may be required. The mass-flow-controllers can also be ordered with lower operating pressures so a lower system pressure can be used. Lower system pressure can increase safety, and increase the saturated vapor concentration of the molecules that are to be admixed in sub-mixing assemblies 254 and 258.

The flow rates of the pneumatic matter through the respective assemblies may be controlled by any of the mass-flow controllers (e.g. flow controllers 230, 232, 246, 248, 250, and 280) associated with the respective assemblies. A computer, such as the computer system illustrated in FIG. 3 (including any software associated therewith), may be used to assist in regulating and/or controlling the various mass flow controllers to regulate and/or control the flow and pressure of the pneumatic matter through any of the assemblies. The mass-flow controllers may be purchased commercially from MKS Instruments, www.mksinst.com, model M100B, part number M100B34CS1BV.

Referring in detail now to FIG. 3, there is seen, by way of illustration only, an exemplary computer system which may comprise and/or operate one or more of the components of FIG. 1 and FIG. 2, or any other component suggested and/or described herein. While other alternatives might be utilized, it will be presumed for clarity sake that control of the components of the systems of FIGS. 1 and 2, and or media device based browser, are implemented in hardware, software or some combination by one or more computing systems consistent therewith, unless otherwise indicated.

Computer system 300 comprises components coupled via one or more communication channels (e.g. bus 301) including one or more general or special purpose processors 302, such as a Pentium®, Centrino®, Power PC®, digital signal processor ("DSP"), and so on. System 300 elements also include one or more input devices 303 (such as a mouse, keyboard, microphone, pen, and so on), and one or more output devices 304, such as a suitable display, speakers, actuators, and so on, in accordance with a particular application.

Computer system 300 also includes a computer readable storage media reader 305 coupled to a computer readable storage medium 306, such as a storage/memory device or hard or removable storage/memory media. Other storage/memory device(s) are broadly illustrated separately as storage 308 and memory 309, which may include hard disk variants, floppy/compact disk variants, digital versatile disk ("DVD") variants, smart cards, partially or fully hardened removable media, read only memory, random access memory, cache memory, and so on, in accordance with the requirements of a particular implementation. The data base(s) (i.e., the storage parameters and other data described herein or illustrated in the drawings) for identifying a substance, molecules, or the odor of a substance, may be stored in storage 308.

The computer system 300 may also further include one or more suitable communication interfaces 307, such as a modem, DSL, infrared, RF or other suitable transceivers, and so on for providing inter-device communication directly or via one or more suitable private or public networks or other components that can include but are not limited to those already discussed.

Figure 5:
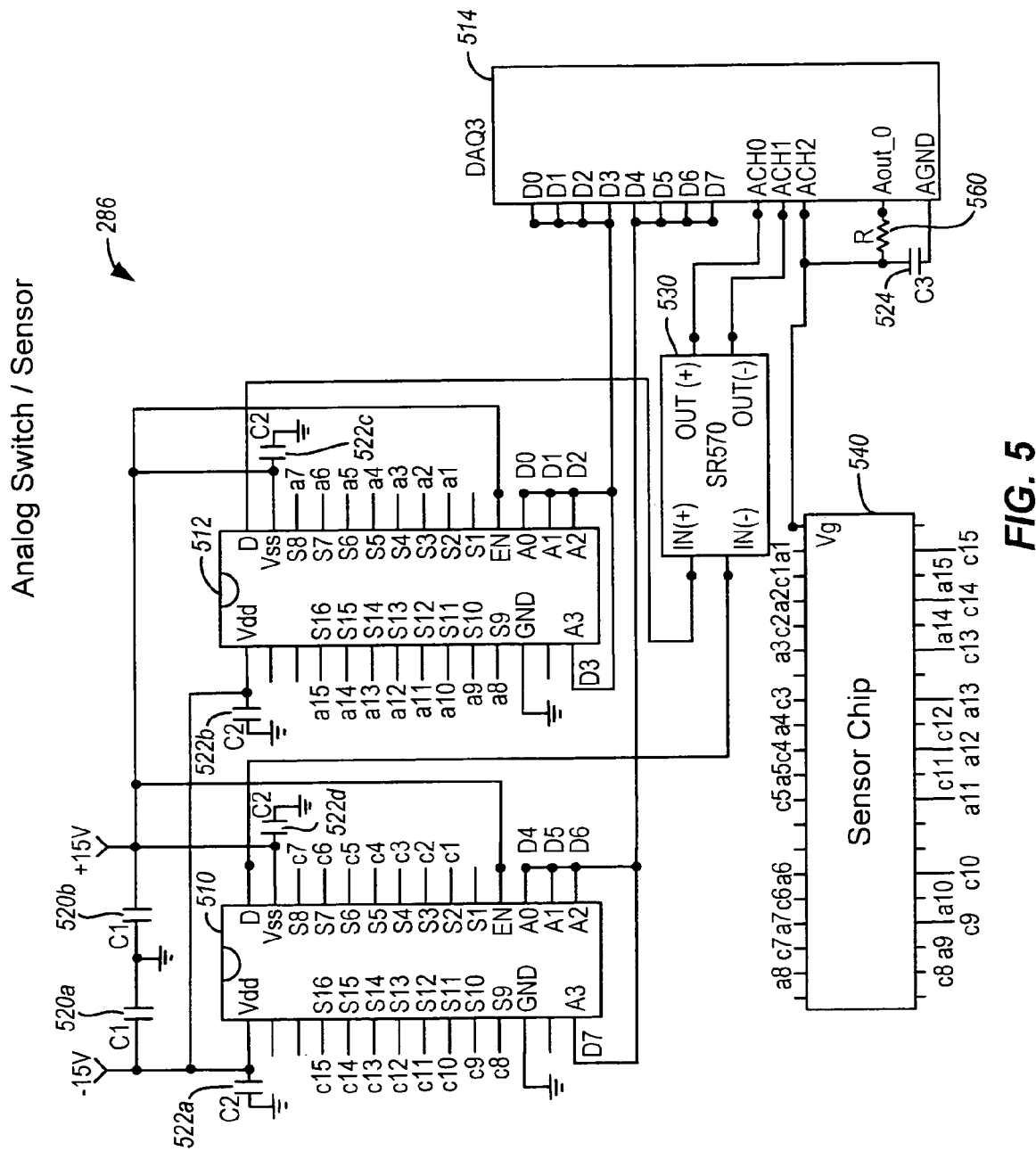
FIG. 5 is an exemplary multiplexer and amplifier circuit for a broad power schematic diagram for embodiments of the present invention.
Figure 6:
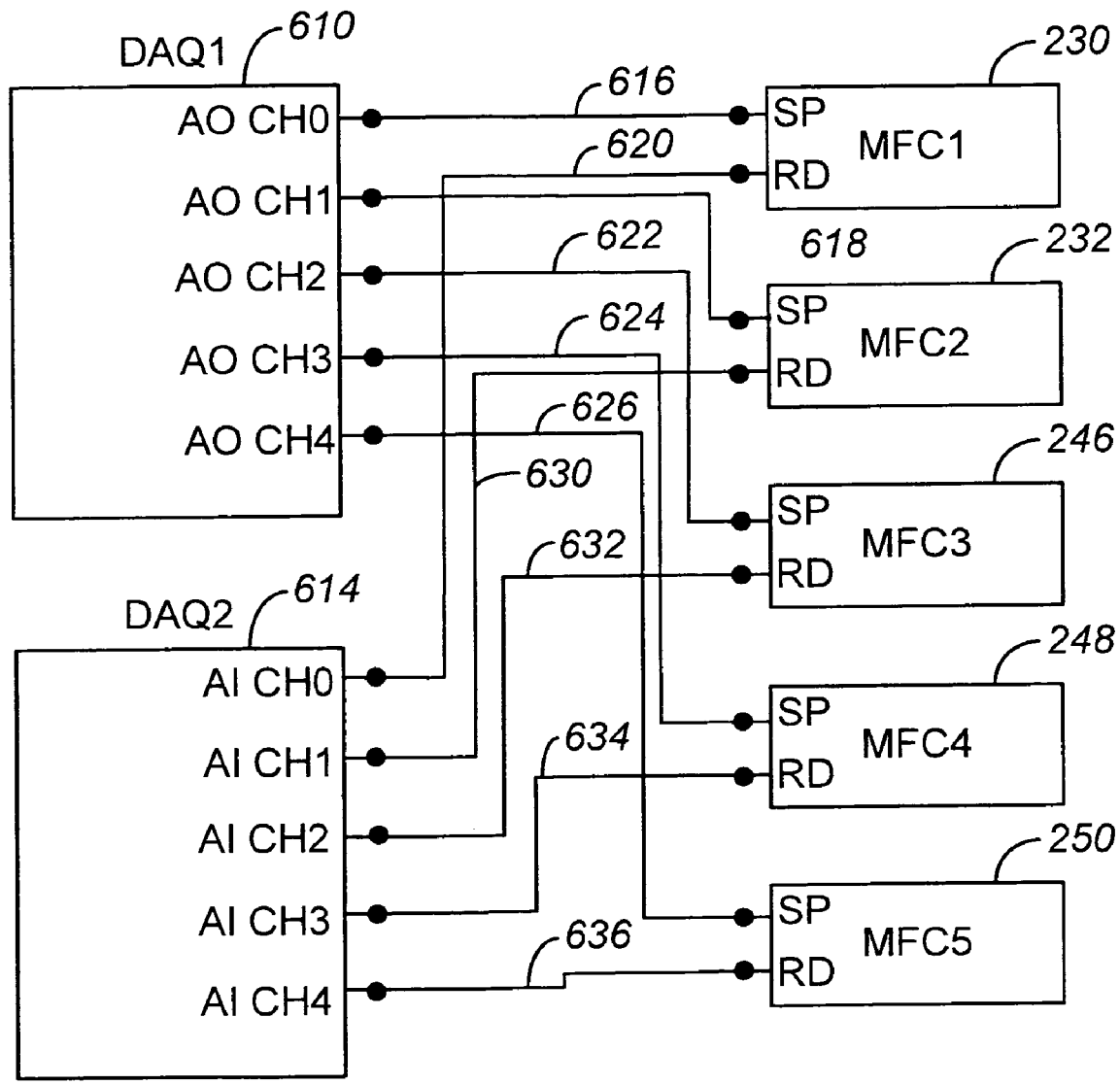
FIG. 6 is an exemplary mass-flow-controller wiring schematic specific power schematic diagram for embodiments of the present invention.

Coupled to the communication channels (e.g. bus 301) are circuit or DAQ (containing digital IN/OUT, and/or analog input, and/or analog output) boards 514, 614, and 610 for sending output demands to and requesting state from various desired components of the various assemblies employed for identifying the signature of molecules in the flowing air and matching the signature with a molecular signature in a data bank (e.g., in storage 308). The DAQ boards 514, 614, and 610 will be further described below, but in physical form are very similar to a video card which removably engages a slot in the motherboard of a computer. For various embodiments of the invention the DAQ boards 514, 614, and 610 slidably, removably engage slots (not shown) in a motherboard (not shown) of the computer system 300, allowing the software for the computer to communicate with the DAQ boards 514, 614, and 610 via the bus 301. Additionally, these DAQ devices may be connected via any pathway to the system bus, e.g. USB, Firewire, SCSI, etc. A cable (not shown) is connected to each of the DAQ boards 514, 614, and 610. Each of the cables contains a plurality of conductors (e.g., 50 to 100 conductors), not all of which are shown in FIGS. 5 and 6. The cables attach to the back of the respective DAQ boards 514, 614, and 610 similar to the manner a monitor is attached to the computer's video card. The cables attach to a break-out box (not shown) that has convenient screw-terminal connections for each of the conductors contained in the cable. Thus, each conductor within the cables is capable of communicating with the computer software via the bus 301. It should be understood that the individual DAQ cards, cables, and break-out boxes are used in present embodiments for cost-effectiveness in the singular prototype. In a large scale production of a device using herein described concepts, the digital I/O, analog input and outputs could be integrated directly into the main computer system. Furthermore, the interconnects between the integrated DAQ and various flow-controllers, sensors, etc could be by any number of cables, single wires, bundled wires, PC-boards, fiber-optic connections, wireless communication methods, or any other means of transmitting a signal from one point to another.

Working memory 310 further includes operating system ("OS") 310*a* components which service and/or assist in adjusting and/or controlling components of embodiments of the present invention, including those components broadly illustrated in the figures of the drawings. Working memory 310 may further include a manager 311 which function for one or more suitable purposes, such as, by way of illustration only, a comparator for comparing identified data from a substance with that in storage 308 to identify odor of a substance, a communicator for correspondences, etc. The working memory 310 may also comprise an application engine 310*c* (e.g., an application link engine, a media device based browser, etc.) for any suitable purpose, a Web client 310*b* for providing substance information to another party, and other programs 312. Working memory 310 components may also include one or more application programs, mobile code, data, and so on for implementing the components of FIGS. 1 and 2 flow diagrams, or any other components described or illustrated elsewhere herein, and which might be stored or loaded therein during use. The particular operating system may vary in accordance with a particular device, features or other aspects in accordance with a particular application (e.g., using Windows, WindowsCE, Mac, Linux, Unix or Palm OS variants, a cell phone OS, IOS or some other proprietary OS, and so on). Various programming languages or other tools can also be utilized, such as those compatible with C variants (e.g., C++, C#), the Java 2 Platform, Enterprise Edition ("J2EE") or other programming languages in accordance with the requirements of a particular application. Such working memory components can, for example, include one or more of applications, add-ons, applets, custom software and so on for conducting but not limited to the examples discussed elsewhere herein. Other programs 312 may, for example, include one or more of security, compression, synchronization, backup systems, groupware code, and so on, including but not limited to those discussed elsewhere herein.

When implemented in software (e.g. as an application program, object, agent, downloadable, servlet, and so on in whole or part), a document system or other component (e.g., such as data used in identifying a substance including its odor, etc) may be communicated transitionally or more persistently from local or remote storage to memory (SRAM, cache memory, etc.) for execution, or another suitable mechanism can be utilized, and elements can be implemented in compiled or interpretive form. Input, intermediate or resulting data or functional elements may further reside more transitionally or more persistently in a storage media, cache or other volatile or non-volatile memory, (e.g., storage device 308 or memory 309) in accordance with a particular application.

Referring in detail now to FIG. 5 for a description of an embodiment of the sensor assembly 286, which may be any suitable sensor assembly employing any suitable sensor technology (polymer sensors, nanotubes, DNA molecules, etc), all capable of analyzing and identifying signature molecules from air containing the molecules and flowing at different flow rates into the sensor assembly 286. More particularly, the embodiments of the sensor assembly 286 may be any suitable sensor assembly which is capable of analyzing and producing a signature that results from the interaction of molecules and the sensor regardless of the particular sensor technology employed. As previously indicated, embodiments of the present invention provide a system and method for preparing molecules for introduction into the sensor assembly 216, and for analyzing the signature that results from the interaction of the molecules and a sensor in the sensor assembly 286. In various embodiments of the present invention, the sensor assembly 286, as best shown in FIG. 5, comprises a pair of multiplexers 510 and 512, electrically coupled together and coupled to a breakout box 514 (National Instruments SCB-100) and to an amplifier 530, and a sensor chip 540 electrically coupled to the breakout box 514 (National Instruments SCB-100). The sensor assembly 286 also comprises capacitors 520*a*, 520*b*, 522*a*, 522*b*, 522*c*, 522*d*, and 524, along with a resistor 560.

Capacitors 522*a*, 522*b*, 522*c* and 522*d* may be 10 μF 50V radial electrolytic capacitors. Capacitors 520*a* and 520*b* may be 0.1 μF 50 V multilayer ceramic capacitors. Capacitor 524 may be a 22 μF 50V multilayer ceramic capacitor. Resistor 560 may be a 2.2 kohmΩ+or −5% carbon film resistor. All GND terminals in FIG. 5 are connected to the common ground of the + and −15V power supply. The a1, a2 . . . a15 labels on multiplexers 510 and 512 correspond to (and connect electrically to) the pins (i.e., a1, a2, . . . a15 and c1, c2 . . . c15) on the sensor chip 540. Capacitors 520a and 520b are bypass capacitors placed where the power wires enter the circuit board upon which chips 510 and 512 are located. Capacitors 522a, 522b, 522c and 522d are bypass capacitors located as close to IC power pins as possible.

In various embodiments of the present invention, the sensor chip 540 could be of any construction that has a change in one or more properties based on the properties of the molecules to be identified. One example (as best shown in FIG. 5) may be a carbon nanotube sensor employed to create the "signature" that is analyzed. The sensor chip 540 may be obtained from any suitable source. The sensor chip 540 could be of any construction that has a change in one or more properties based on the properties of the molecules to be identified. Generally, the molecules carried in the air elicit a change in the sensor chip 540 which creates the 'molecular signature'. Additionally, it should be understood that although this embodiment only utilizes a single sensor or sensor type, it is generalized that one or more of the same or different sensors may be used in an application. This allows for increased sensitivity for different molecules. For example, some molecules could be easily detectable with a nanotube while other molecules may all look the same to the nanotube and in this case we could use a second type of sensor to augment the nanotube for better sensitivity. Thus, embodiments of the invention include the use of two or more sensors, with each sensor having a different sensitivity. One sensor, such as sensor chip 540, would have one sensitivity level, while another sensor (e.g., a carbon-black resistor or polymer sensor) employed contiguously to the sensor chip 540 would have a greater sensitivity (i.e., a sensitivity that is more than, or more sensitive than, the sensitivity of the sensor chip 540 and capable of identifying molecules that the sensor chip 540 could not).

The carbon nanotubes sensors are located on a silicon die. This die is placed on a 40 pin dual-in-line-package (DIP). The contacts for the nanotube sensors are wired bonded to the pins of the 40 pin DIP. This configuration allows the nanotubes to be conveniently indexed via the pins of the DIP.

The nanotube sensors are functionally similar to a field-effect-transistor. These three terminal devices have a gate, an anode, and a cathode. The voltage applied to the gate controls the conductivity between the anode and cathode. However, with the nanotube, this conductivity is also affected by what is in the environment (i.e., different types of molecules being transported in the air). All of the nanotubes in the DIP share a common gate (the silicon substrate), therefore there is only one terminal (i.e., terminal Vg on sensor chip 540) to control the gate voltage. The hardware and software interface is based on this common gate and the various pairs of anodes and cathodes (e.g. on sensor chip 540 anodes a1 . . . a15 and cathodes c1 . . . c15) to address the nanotubes. To measure the conductance versus gate-voltage relation of a particular nanotube a bias voltage (Vb) is applied between the anode and cathode and the current is measured Ohm's law $V=I*R$) is used to convert voltage (V) and current (I) to resistance ($R=V/I$).

The applied bias voltage induces a current in the nanotube. The induced current is measured by the upstream hardware and software. The gate voltage is modulated by a triangle waveform, or any suitable waveform such as a sine wave or even a constant voltage, generated by the upstream hardware and software. This triangle waveform is created by discrete points at a particular update frequency. For the NI-6031E (i.e., DAQ3 514) the maximum update rate is 100 k samples/sec. This discrete updating of the gate voltage signal causes unwanted noise at the update frequency. A low-pass filter with a cutoff frequency of 1 kHz is installed at the source of the waveform (i.e., resistor 560 and capacitor 524). This allows the gate voltage to sweep relatively fast (up to approximately 1 kV/sec) and effectively eliminates the waveform update noise. If a faster gate voltage waveform is used, the low-pass filter should be changed accordingly (at the expense of slightly higher noise).

For embodiments of the present invention, amplifier 530 is a single current-to-voltage amplifier for addressing and tending to the nanotube sensor in the sensor chip 540. However, for various embodiments of the invention when more than one nanotube sensor (or additional more sensitive sensors) is/are employed, more than one amplifier may be used, with each amplifier assigned to a sensor (i.e., a nanotube sensor or a more sensitive sensor). With the single amplifier 530 (SR570), an analog multiplexer circuit comprising the pair of multiplexers 510 and 512 is used to select the nanotube sensor in the sensor chip 540. Multiplexers 510 and 512 are analog multiplexer integrated circuits (IC), ADG406 (Analog Devices, Norwood Mass., www.analog.com). Each of the multiplexers 510 and 512 (ADG406) switches one of sixteen inputs (S1 . . . S16) to a common output (D) as determined by its 4-bit binary address lines (A0 . . . A3). The binary address lines are controlled by the upstream DAQ hardware (e.g., circuit board 514) and the computer software. One multiplexer ADG406 (i.e., multiplexer 512) is connected to all the anodes (i.e., a1, a2 . . . a15) in the sensor chip 540 and the second multiplexer ADG406 (i.e., multiplexer 510) is connected to all the cathodes (i.e., c1, c2 . . . c15) in the sensor chip 540. The common (D) output from the two multiplexers (ADG406s) 510 and 512 are connected to the current-to-voltage amplifier 530 (SR570, Stanford Research Systems, Sunnyvale, Calif. www.thinksrs.com). The amplifier 530 provides the anode-cathode bias voltage. It should be understood that although the commercially available SR570 is shown in the present embodiment, any suitable conditioning circuit can be used. One such circuit (not-shown) would be a pair of operational amplifiers ("op-amps"), one configured in an 'inverting' configuration and the other in a 'non-inverting' configuration and the sensor placed between the inverting terminals of the two op-amps. Additionally, if the sensor output was of different physical form, for example photons, voltage, or current, the necessary conditioning circuit would be used so that the physical changes were properly converted to voltage levels measurable by the DAQ device.

Referring now to FIG. 6, there is seen a schematic diagram of the control assembly for controlling the mass-flow controllers 230, 232, 246, 248, and 250. As shown in FIG. 6, DAQ boards 614 and 610 are broadly electrically coupled to mass-flow controllers 230, 232, 246, 248, and 250 via conductors 616, 620, 622, 624, 626, 630, 632, 634, and 636 for sending output commands to appropriately control the flow of air. DAQ boards 614 and 610 receive software signals via bus 301 (see FIG. 3) for metering and/or controlling air flow for controlling humidity and molecular concentration in the air. As previously indicated humidity and temperature sensor 284 continually monitors the temperature of the mixture of air and molecules entering the sensor assembly 216, and if the humidity is detected as being outside of ambient conditions, appropriate signals are sent via the computer software to the DAQ boards 614 and 610. More specifically, the humidity and temperature sensor 284 regulates humidity of the air leaving the junction by providing feedback for a software PID loop associated with a computer assembly 300 that regulates the ratio of humidified air from humidifier 234 to the warm air flowing from controller 232. If the humidity and temperature sensor 284 detects that the prepared molecules/warm/humidified air has insufficient or too much humidity, a signal (i.e., feedback) from a software PID loop is transmitted to the flow controllers 230 and 232 via the DAQ boards 614 and 610 to adjust the ratio of dry and wet air when mixed together at juncture 237.

DAQ boards 614 and 610 are also capable of receiving software signals via bus 301 for metering and/or controlling air flow for controlling molecular concentration in the air. Any device that can suitable measure concentration, such as a photo-ionization or flame-ionization gas analyzer, a mass-spectrometer, a gas-chromatograph, etc, may be employed for various embodiments of the present invention. Such device is capable of continually monitoring the concentration of the molecules in the prepared molecules/warm/humidified air entering the sensor assembly 216, and if the concentration is not as desired (i.e., either too low or too high), appropriate signals are sent via the computer software to the DAQ boards 614 and 610 for sending signals to the mass-flow controllers 246, 248, and 250 to adjust the mixing at juncture 269 of the prepared molecules/warm/humidified air flowing through conduit 276 with the warm/humidified air flowing through value 272.

For various embodiments of the present invention, the analog multiplexer circuit, data acquisition hardware, and gate voltage generation, are controlled by LabView software and several LabView Virtual Instruments (National Instruments, Austin, Tex. www.ni.com). LabView is a graphical programming language and a Virtual Instrument (VI) is an executable program or routine that runs in the LabView environment. Any program language that can access and control the hardware acquisition boards (C++, Matlab, etc) may be used instead of the LabView software. As previously indicated, the three circuit boards 514, 610 and 614 (i.e., three PCI cards) are slid into slots of the motherboard of the computer assembly 300 of FIG. 3 in order to interface the software with the sensor assembly 286, the mass-flow controllers, and associated electronics. The first board (DAQ1), circuit board 610, is a National Instruments NI-6704. As previously indicated, this board has 16 analog output channels that are used to send analog control commands to the mass-flow controllers 230, 232, 246, 248, and 250. The other two boards (DAQ2 & DAQ3), circuit boards 514 and 614, are model NI-6031E. These boards have 64 analog input and 2 analog output channels (ACHs). DAQ2, circuit board 614, reads the analog voltages from the controllers 230, 232, 246, 248, and 250 at a low frequency (around 20 Hz). DAQ3, circuit board 514, reads the gate voltage and SRS-amplifier output at its maximum frequency (100 kHz multiplexed). Circuit board 514 is used to maximize the sensor and gate voltage-sampling rate. All three circuit boards have an 8-bit digital I/O port.

Figure 10:
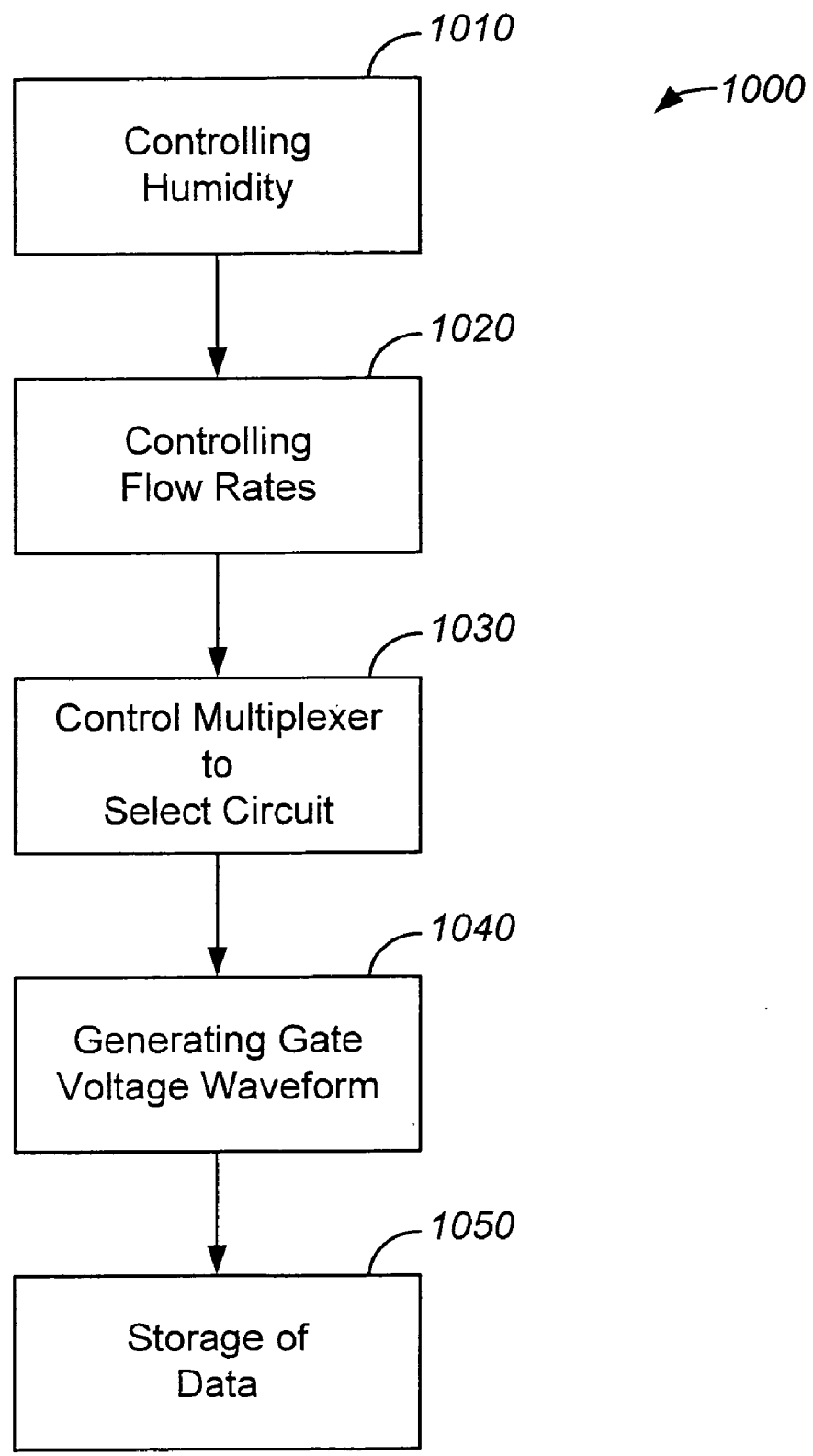
FIG. 10 is a schematic software block flow diagram represented by blocks for controlling humidity of the air, controlling the flow rates, controlling the multiplexers to select a circuit, generating a gate voltage waveform, and for storage of data.

Referring in detail now to FIGS. 10-15 there is seen software block flow diagrams for illustrating the preparation and delivery of air to the sensing assembly 216 and for identifying the signature molecules in the sensing assembly 216. The LabView software is designed in functional blocks that are executed in concert to maximize automation of data collection. There is seen in FIG. 10 schematic software block flow diagram, generally illustrated as 1000, including block 1010 representing controlling humidity of the heated air, block 1020 representing controlling the flow rates of the air (i.e., setting the molecule flow rate and concentration), block 1030 representing controlling the multiplexers to select a circuit (i.e., controlling the analog multiplexer to select the nanotube sensor), block 1040 representing generating a gate voltage waveform, and block 1050 representing the storage of data (i.e., acquiring data and saving it to a disk or hard dive).

Figure 11:
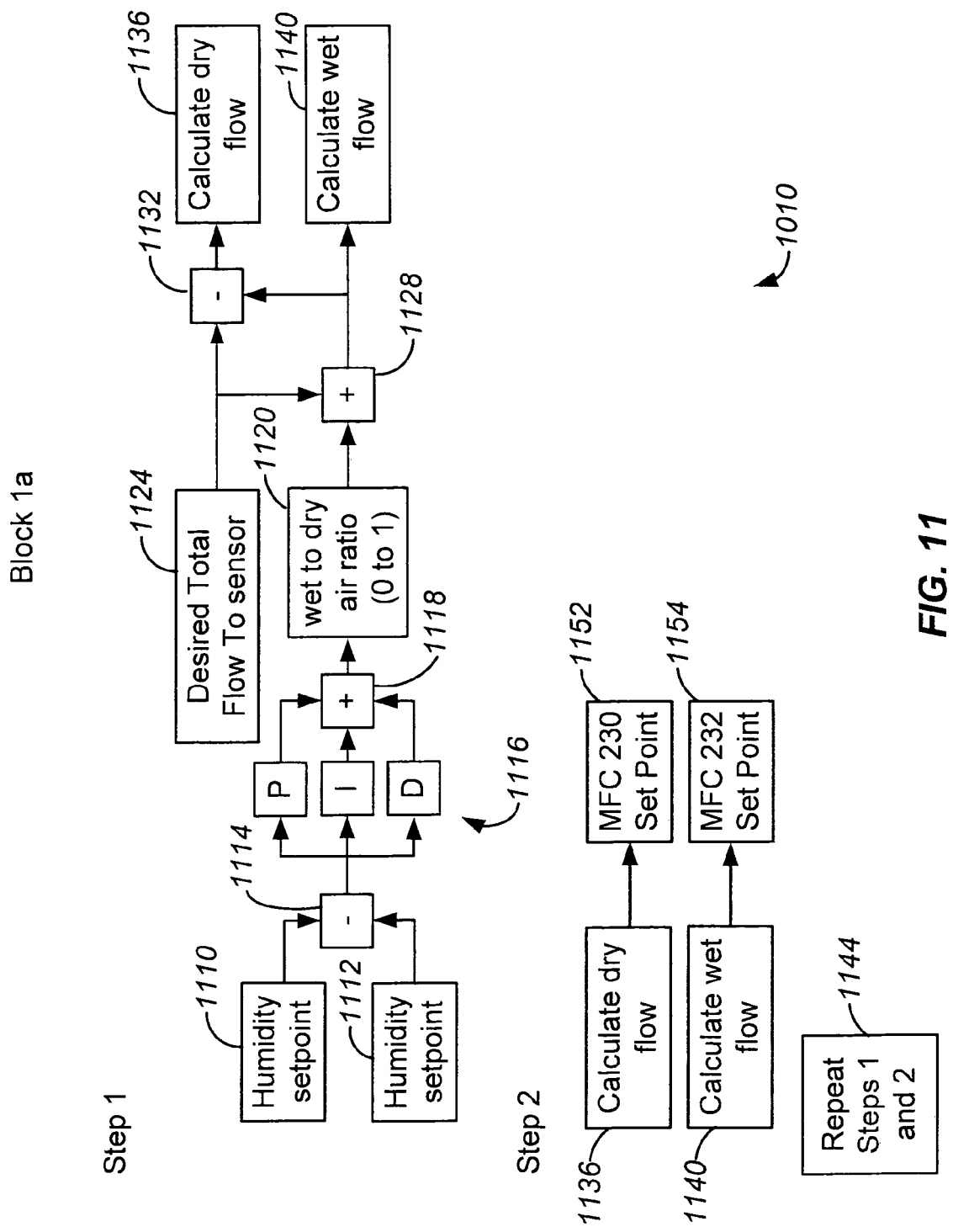
FIG. 11 is a schematic software block flow diagram for controlling humidity of the air.
Figure 12:
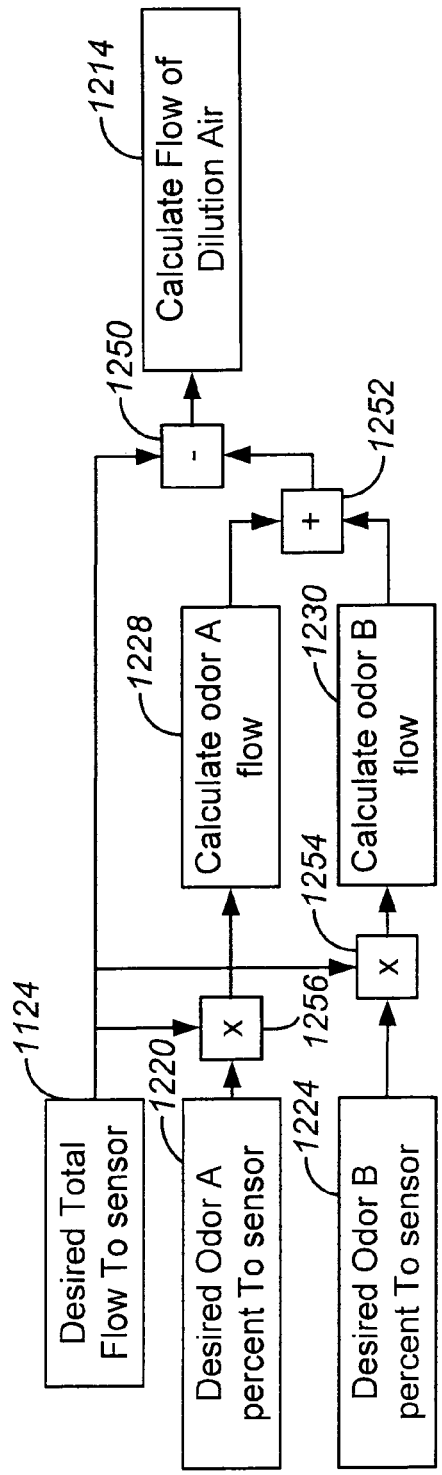
FIG. 12 is a schematic software block flow diagram for controlling the flow rates of the air to the sensor.
Figure 12:
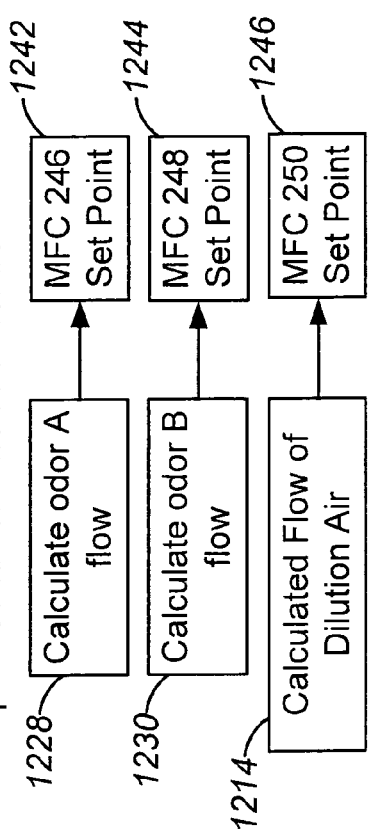

Referring now to FIGS. 11-12, there is broadly illustrated a block flow diagram of how the software handles communication with the mass-flow controllers (MFCs). The MFCs regulate the air flow to the sensor assembly 216 to control concentration, total air flow, and humidity. The MFCs are connected to circuit board 610 (DAQ1) and circuit board 610 (DAQ2). Circuit board 610 sends voltage signals to the MFCs to control flow rates, and circuit board 614 measures the flow reading from the MFCs. A subroutine illustrated in FIG. 11 is the PID loop 1116 that regulates the humidity. As previously indicated, the ratio of the air flow through flow controllers 230 and 232 is adjusted so the output humidity matches the set point humidity. The procedure is a continuous procedure to ensure proper regulation of the humidity.

Referring more specifically now to FIG. 11 there is seen humidity set point 1110 (the desired humidity of the prepared molecules/warm/humidified air) and humidity reading 1112 from the sensor 284. The humidity set point 1110 and the humidity reading 1112 is subtracted from the desired humidity set point 1110 set point to create an error represented by block 1114. This error value is then applied to a PID function, generally illustrated as 1116 and which repeats every 0.1 seconds (10 hz), representing the Proportional, Integral, Derivative functions whereby the output of each function is indicative of the function name. The Proportional function returns a value that is proportional to the error value. The Integral function returns a value that is proportional to the integral of the error. The Derivate function returns a value that is proportional to the derivate of the error. The control constants (Kp, Ki, and Kd) are determined for the actual system and cannot be pre-determined. Generally, one initially tries values of Kp that allows the feedback to moderately control the system while keeping Ki and Kd fixed at zero. After a value of Kp is determined, the value of Ki is slowly increased until a value is obtained that allows the set point to be matched but is not so high as to allow oscillations in the feedback. Last, Kd is chosen so the system can quickly respond to perturbations of the system. In the described system, there is little perturbation and stability is more important than speed so Kd is rarely non-zero.

The values from the three functions are summed at block 1118. This number should be between 0 and 1 and the software is written to force the value to within these limits if it is not. This value is the ratio of wet to dry air as represented by block 1118. The value is then multiplied (as represented by block 1128) by the final flow rate to the senor 284, resulting in the calculated flow rate of wet air represented by block 1140. For determination of the flow of dry air, the amount of wet air flow of block 1140 is subtracted (represented by block 1132) from the total desired total flow rate to sensor 284 (represented by block 1124), resulting in the calculated dry flow of block 1136. For example, if the final desired flow rate to sensor 284 is 10 liters-per-minute and the ratio is 0.6, then the calculated wet flow (block 1140) would be 6 liters-per-minute and the calculated dry flow (block 1136) would be 4 liters-per-minute.

After the calculations represented by blocks 1136 and 1140 are completed, the values are sent to mass-flow-controllers 230 and 232, respectively represented by blocks 1152 and 1154. This process of adjusting the flow rates depending on the humidity reading repeats continuously, as represented by block 1144 ("Repeat Steps 1 and 2"), while the sensor 284 is receiving air. Although experience will dictate the actual value, a frequency of 10 Hz is likely to be adequate to properly regulate the humidity.

Referring in detail now to FIG. 12, an exemplary flow diagram for setting the molecule flow rate and concentration for two exemplary substances, A and B. The desired flow rate of odor A (block 1228) and the desired flow rate of odor B (block 1230) are determined by multiplying (represented respectively by blocks 1256 and 1254) the respective desired percentage of odor A to sensor (block 1220) and desired percentage of odor B to sensor (block 1224) by the desired final total flow rate to sensor (block 1210). The required amount of dilution (filler) air (block 1214) is determined by subtracting the sum (block 1252) of the [calculated odor A flow (block 1228) and the calculated odor B flow (block 1230)]. These three values respectively represented by blocks 1228, 1230 and 1214 are then passed to the mass-flow controllers 1228, 1230 and 1214, respectively.

Figure 13:
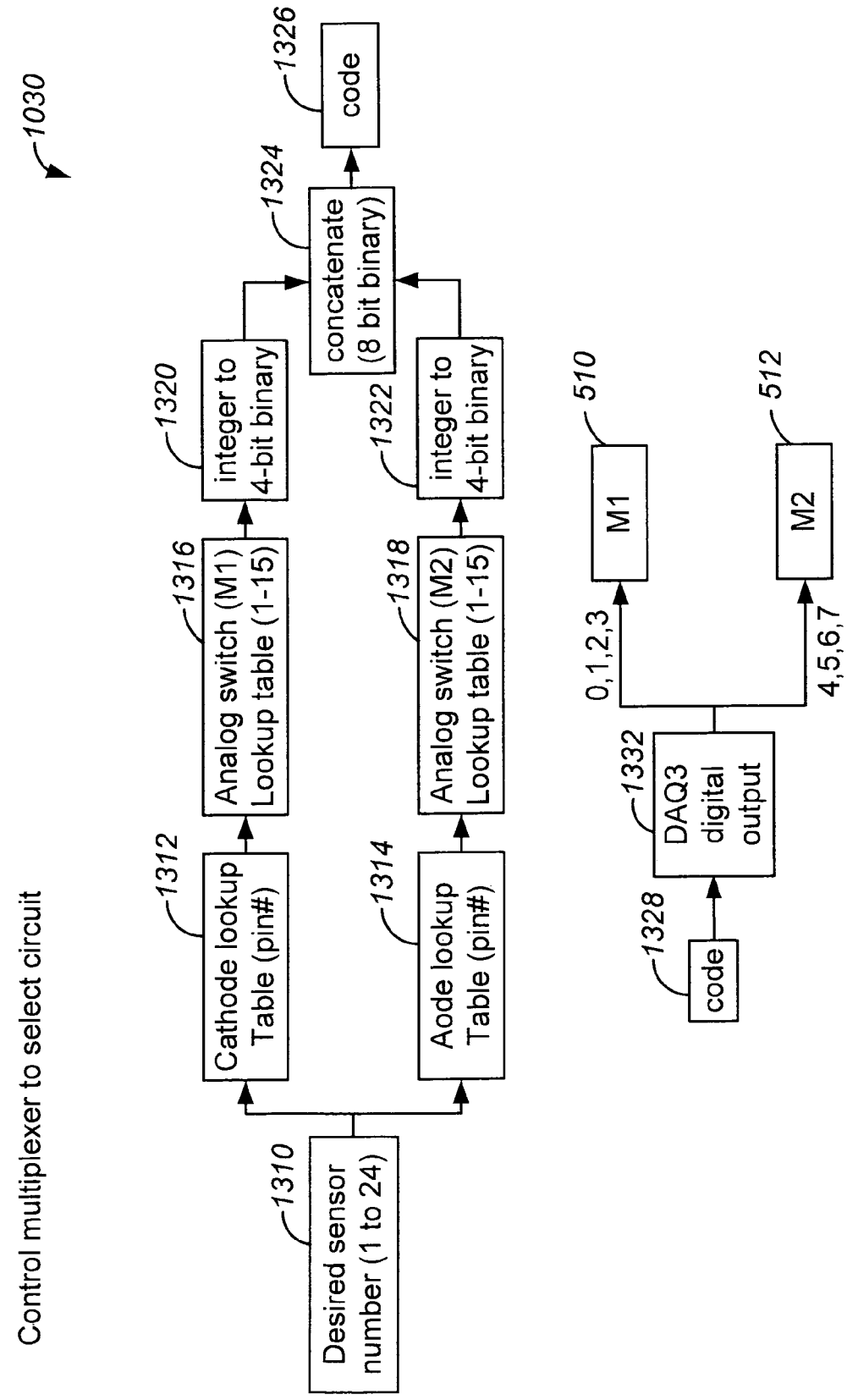
FIG. 13 is a schematic software block flow diagram for controlling the multiplexers to select a circuit.

Referring now to FIG. 13, there is more specifically seen a schematic software block flow diagram of the analog multiplexer control. The analog multiplexer for selecting a circuit or nanotube sensor is controlled by 8 digital outputs from circuit board 610 (DAQ1). The first four lines control the anode-connected switch and the second four control the cathode-connected switch. The software contains a 24×2 element matrix that represents the connections between the particular anodes and cathodes. For example, anode 3 is connected to cathodes 2 and 4 by two different nanotubes. By choosing one of the 24 rows, the software indexes a particular nanotube sensor. The integers within the particular row are converted to 4-bit binary and then sent to circuit board 610 (DAQ1) which updates the physical connections to the analog multiplexers. The circuit board 610 (DAQ1) updates the digital output port every time a new row is selected.

More particularly and continuing to refer to FIG. 13, the desired sensor number (block 1310) is passed to cathode lookup table (block 1312) and to anode lookup table (block 1314) that provide the package pin numbers for the desired nanotube sensor. These pin numbers are then passed to another pair of lookup tables (blocks 1316 and 1318) that convert the pin numbers into their respective analog switch numbers (multiplexer (M1) 510 and multiplexer (M2) 512). For example, the first sensor is between pins 2 and 3 and pin 2 maps to analog switch M1:1 and pin 3 maps to M2:1. The two switch values of blocks 1316 and 1318 are then respectively converted to a 4-bit binary number represented by blocks 1320 and 1322. For example, switch 1 is 1000 and switch 15 is 1111. The two 4-bit codes are concatenated at block 1326, coded at block 1328, and then sent to the circuit board 514 (DAQ3) digital output represented by block 1332 in which the two analog switch integrated circuits (multiplexer 510 (M1) and multiplexer 512 (M2)) are wired. The first four digital lines (0,1,2,3) are connected to multiplexer 510 (M1) and the last four lines (4,5,6,7) are connected to multiplexer 512 (M2).

In the current embodiment, the sensor used is a carbon nanotube placed on a silicon substrate. As described earlier, the nanotube behaves similarly to a field-effect-transistor (FET). A FET, or nanotube sensor, is a three terminal device: anode, cathode, and gate voltage. In both devices, the conductance (e.g. the degree of electron mobility) between the anode and cathode is partially determined by the voltage applied to the gate terminal. Hence there is a relationship between conductance and gate voltage that is a description of how the device behaves. However with the nanotubes, the conductance is also affected by the environment (e.g. molecules adjacent to the surface of the nanotube that can either donate or borrow electrons from the nanotube). The degree to which a molecule donates or borrows electrons is based on many factors including but not limited to, polarity, shape, size, charge, etc. As the gate voltage of the nanotube changes, the degree to which environmental molecules effect the nanotube changes. This effect is different than the transistor-like effect of conductance change as a function of gate-voltage (e.g. low conductance ("off") at negative gate voltage and high conductance ("on") at positive gate voltage). If the gate voltage is negative or positive this tends to favor either the donating or borrowing of electrons from environmental molecules. Thus by changing the gate voltage of the nanotube in a relatively slow and methodical manner, it is possible for the nanotube to be selective of different types of molecules as a function of gate voltage. This selection, although not completely understood, is generally though to be based on the electrical charge and polarity of the molecules. In other words, by sweeping the gate voltage the nanotube provides more information than if it was at a fixed voltage.

It is to be understood that the sensors respond differentially in the presence of different molecules, in either a time variant or invariant fashion. In the case of time variant responses (or similarly, time invariant but multidimensional responses, such as if multiple properties of a sensor can be read), as in the present embodiment or an embodiment with polymer sensors, the time sequence of the response forms a high dimensional response to the characteristics of the molecules to be identified. Thus, either the response of a single sensor or multiple sensors may be combined to create a high dimensional response space which, when suitably analyzed, can be used to establish molecular identity. In the case of time invariant responses, wherein the response of the sensor is a fixed univariate response multiple different sensors with sufficiently different responses can also be combined to produce a high dimensional response space, which when suitably analyzed can be used to establish molecular identity.

Figure 14:
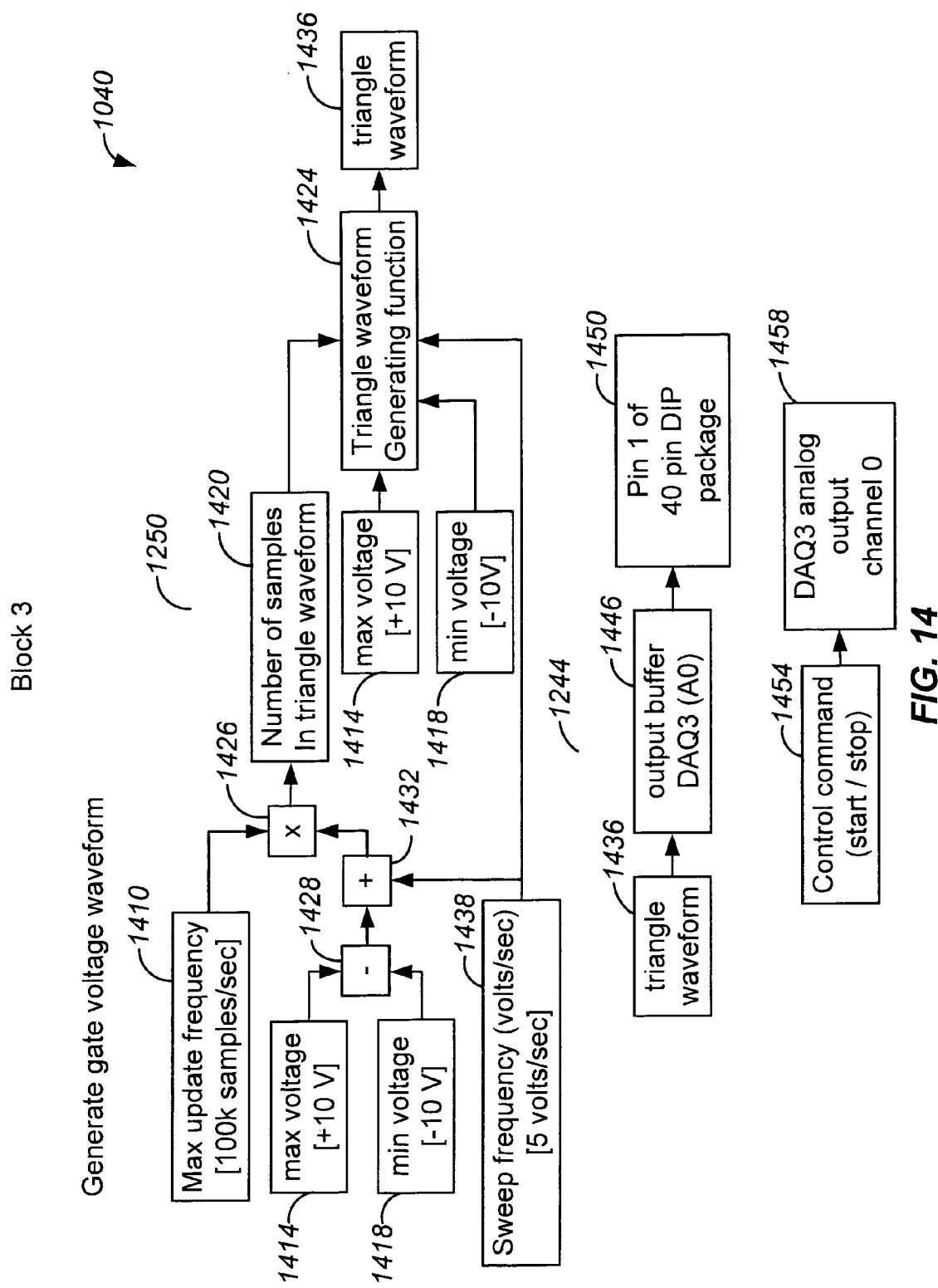
FIG. 14 is a schematic software block flow diagram for generating a gate voltage waveform.

Referring now to FIG. 14, there is more specifically seen a schematic software block flow diagram for generating a gate voltage waveform. Circuit board 514 (DAQ3) handles the generation of the gate voltage. The software block flow diagram of FIG. 14 allows the user to choose the voltage range (typically −10 to +10 volts) and the sweep frequency (e.g., 5 volts per second). With this information, the software creates a triangle waveform and stores it on the analog output hardware buffer of the circuit board 514 (DAQ3). The circuit board 514 (DAQ3) is initialized to update as rapidly as possible (100 k samples/second). Once this information is stored in the memory of the circuit board 514 (DAQ3), the software only needs to send START and STOP commands to control the waveform generation. The START command puts the circuit board 514 (DAQ3 board) in continuous output mode in which it outputs the data buffer at the specified output rate. Once the STOP command is received, the circuit board 514 (DAQ3 board) terminates the output.

More particularly and continuing to refer to FIG. 14, parameter max voltage (block 1414) and min voltage (block 1418) are subtracted (block 1428) and then divided (block 1432) by parameter sweep frequency represented by block 1438 to subsequently by multiplied (block 1426) by the multifunction I/O boards maximum (or desired) output rate (block 1410) resulting in the number of samples per triangle waveform (block 1420). The value of block 1420, the max voltage parameter of block 1414 and the min voltage parameter of block 1418 are passed to the triangle waveform generation function of block 1424 which in turn returns a variable containing the triangle waveform represented by block 1436. The waveform variable of block 1436 is stored in the output buffer (block 1446) of circuit board 514 (DAQ3) for analog output channel 0. Analog output 0 is connected to the gate voltage pin (pin 1) of the 40 pin DIP package (block 1450). A software command represented by block 1454 can then be sent to the circuit board 514 (DAQ3 board) to start or stop the generation of the waveform from channel 0 to pin 1 (block 1458).

Figure 15:
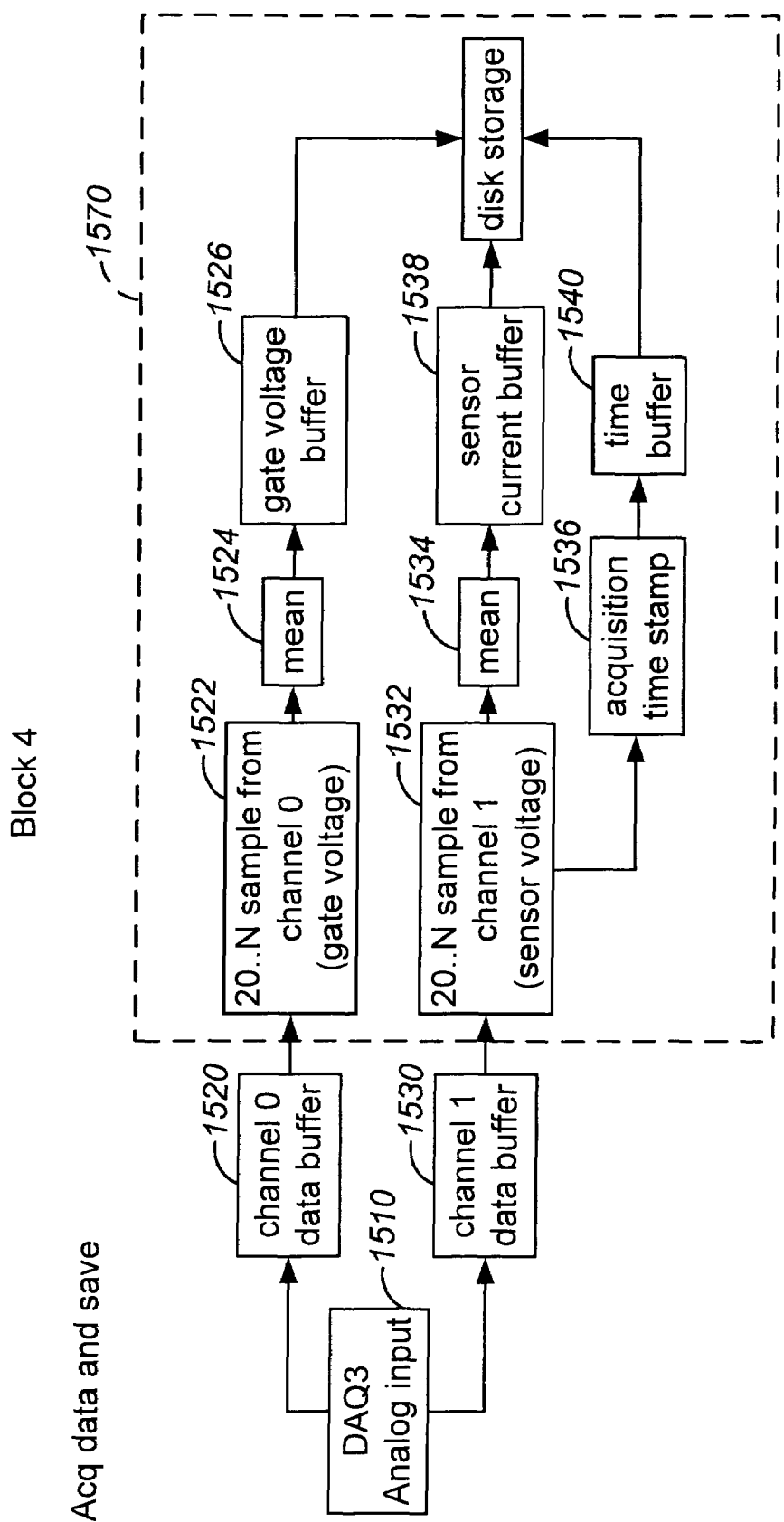
FIG. 15 is a schematic software block flow diagram for storage of data.

FIG. 15 is a schematic software block flow diagram for storage of data, more specifically for controlling the acquisition of the gate voltage and sensor current data. Because the gate voltage output waveform update is set in a 'free running mode', it is necessary to measure the gate voltage at the same time as the sensor current. The software is written to operate as quickly as possible to maximize sampling frequency. The data is acquired and stored in a buffer and the software reads from the buffer. Each read from the buffer contains many samples and these are averaged together. The averaged data, along with acquisition time stamp, are stored in a second buffer. After the pre-determined amount of data is acquired the data acquisition is paused and the second buffer is saved to disk.

Figure 18:
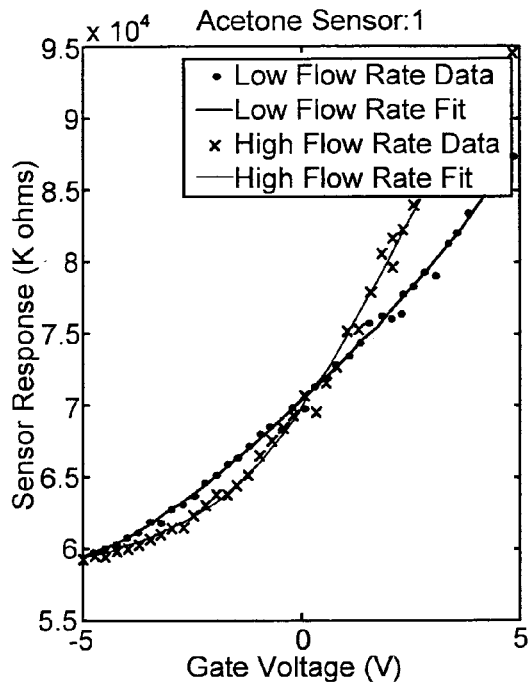
FIG. 18 is a graph of sensor response vs. gate voltage (Volts) including a fitted polynomial for acetone.
Figure 19:
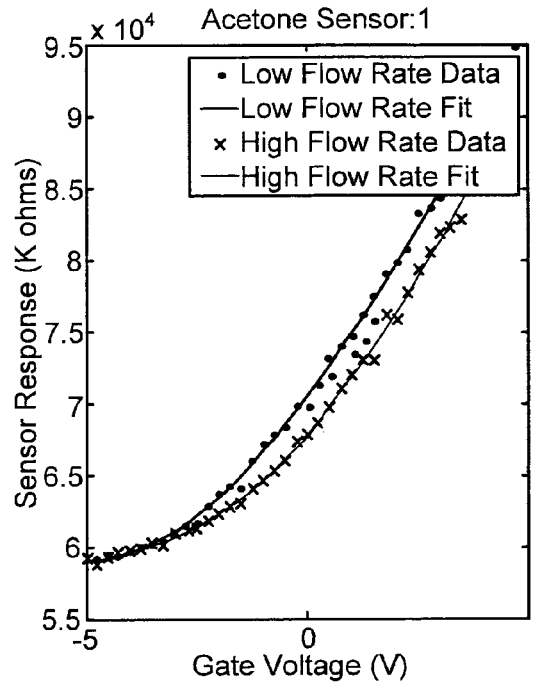
FIG. 19 is another graph of sensor response vs. gate voltage (Volts) including a fitted polynomial for acetone.
Figure 20:
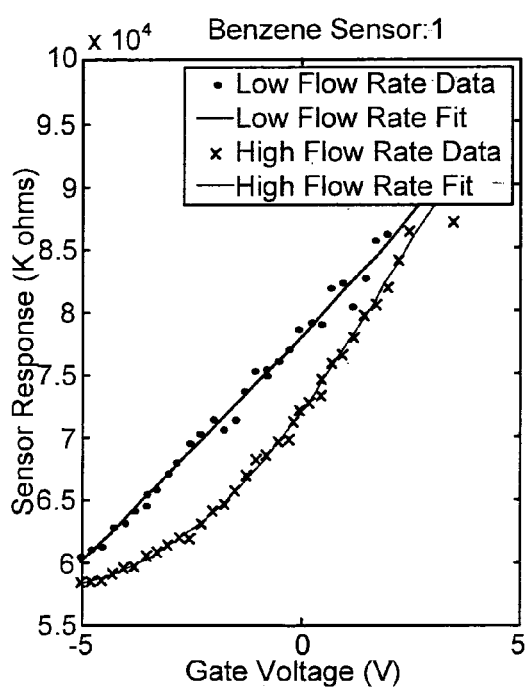
FIG. 20 is a graph of sensor response vs. gate voltage (Volts) including a fitted polynomial for benzene.
Figure 21:
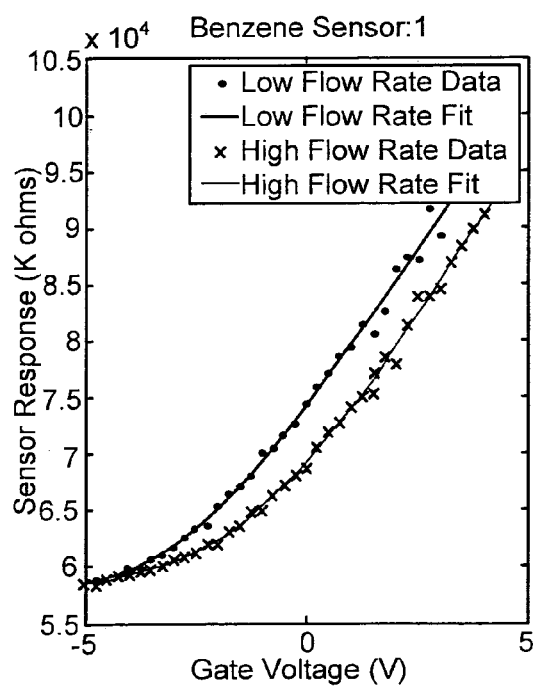
FIG. 21 is another graph of sensor response vs. gate voltage (Volts) including a fitted polynomial for benzene.

More particularly and continuing to refer to FIG. 15, analog input board 514 (DAQ3 board) samples two channels (0 and 1) at 50 kilosamples-per-second and the data is stored in the two buffers represented by blocks 1520 and 1530. The amount of data in the respective buffers increases at the rate of 50 k/sec until the software queries the respective buffers and extracts all of the data. If there are less than 20 data values in any buffer, the software waits until that buffer size contains 20 samples. When the software extracts the samples, the samples are removed from the buffers; and thus the buffers become empty until the circuit board 514 (DAQ3 board) stores more data in the buffers. The extracted data from buffers, represented by blocks 1522 and 1532, is then averaged at blocks 1524 and 1534, then stored in a separate pair of buffers represented by blocks 1526 and 1538. A third buffer at block 1540 is created by extracting the data acquisition time stamp (block 1536) associated with the sample (block 1532) extracted from the channel 1 data buffer (block 1530) each iteration. The three buffers represented by blocks 1526, 1538 and 1540, thus then contain an average measure of the gate voltage and sensor current for a short time interval that begins at time T where T is the value of the extracted timestamp (block 1536). The three buffers represented by blocks 1526, 1538 and 1540 are stored on the computer's hard disk drive (block 1550). As seen in FIG. 15, the assembly surrounded by the broken/dashed lines represented by 1570 indicates the loop that transfers 50 k/s data from the circuit board 514 (DAQ3 board), averages the data and saves to disk storage (block 1550). This loop is limited in its execution rate for a variety of factors (system overhead, size of buffers, CPU speed, hard drive speed, etc) and thus it operates at a much slower rate than the data acquisition board is acquiring data. For reference, the system used to collect data for the best mode presented below was a Macintosh PPC 400 Mhz with 256 MB ram and the second loop operated at approximately 25 Hz (or approximately 50 data points per gate-voltage triangle wave, see FIG. 18). However, with the circuit board 514 sampling at a much higher rate the signal noise is reduced with the signal averaging that is performed for each of these data points.

Figure 16:
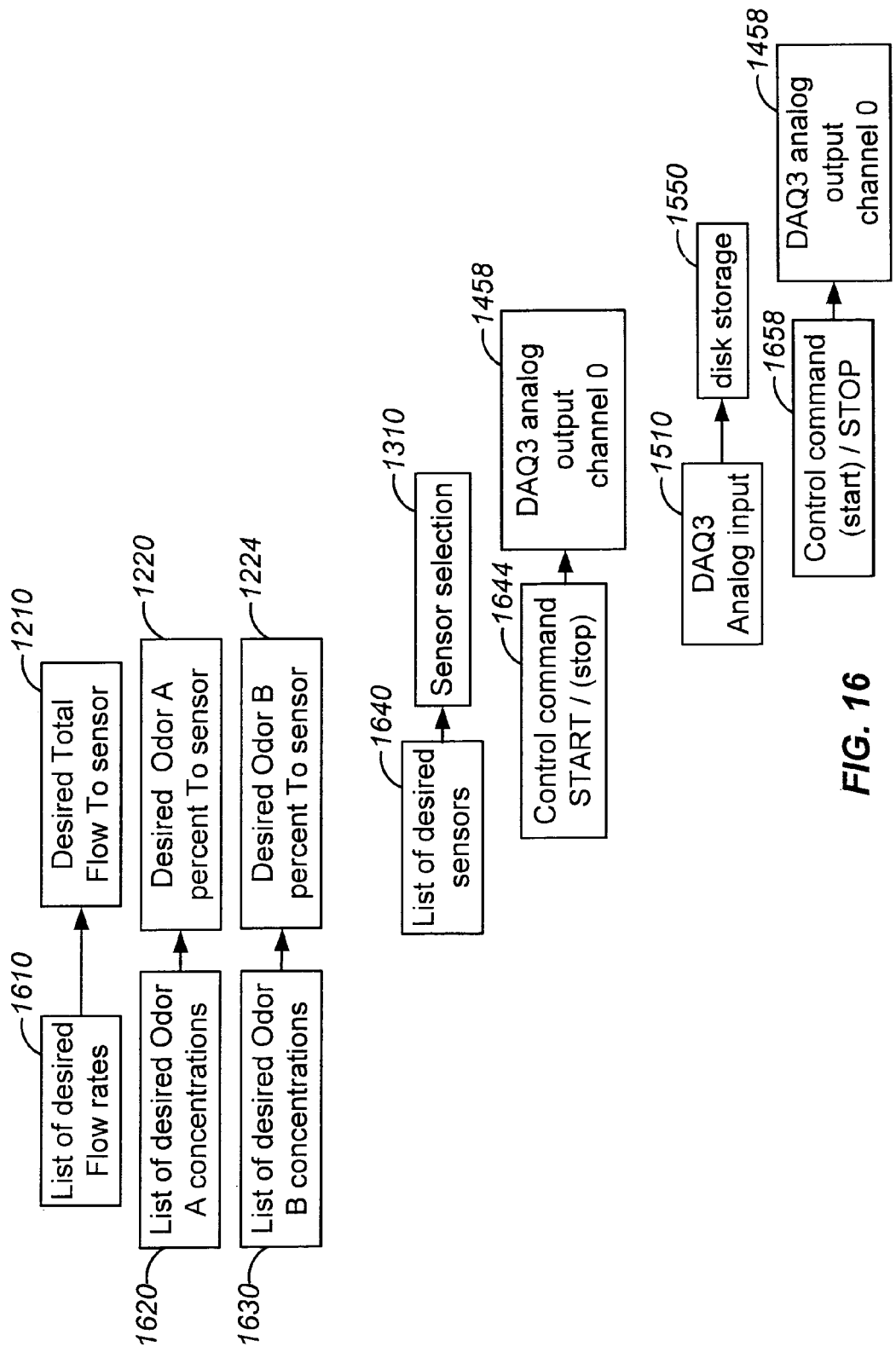
FIG. 16 is a schematic block flow diagram for software layout.
Figure 17:
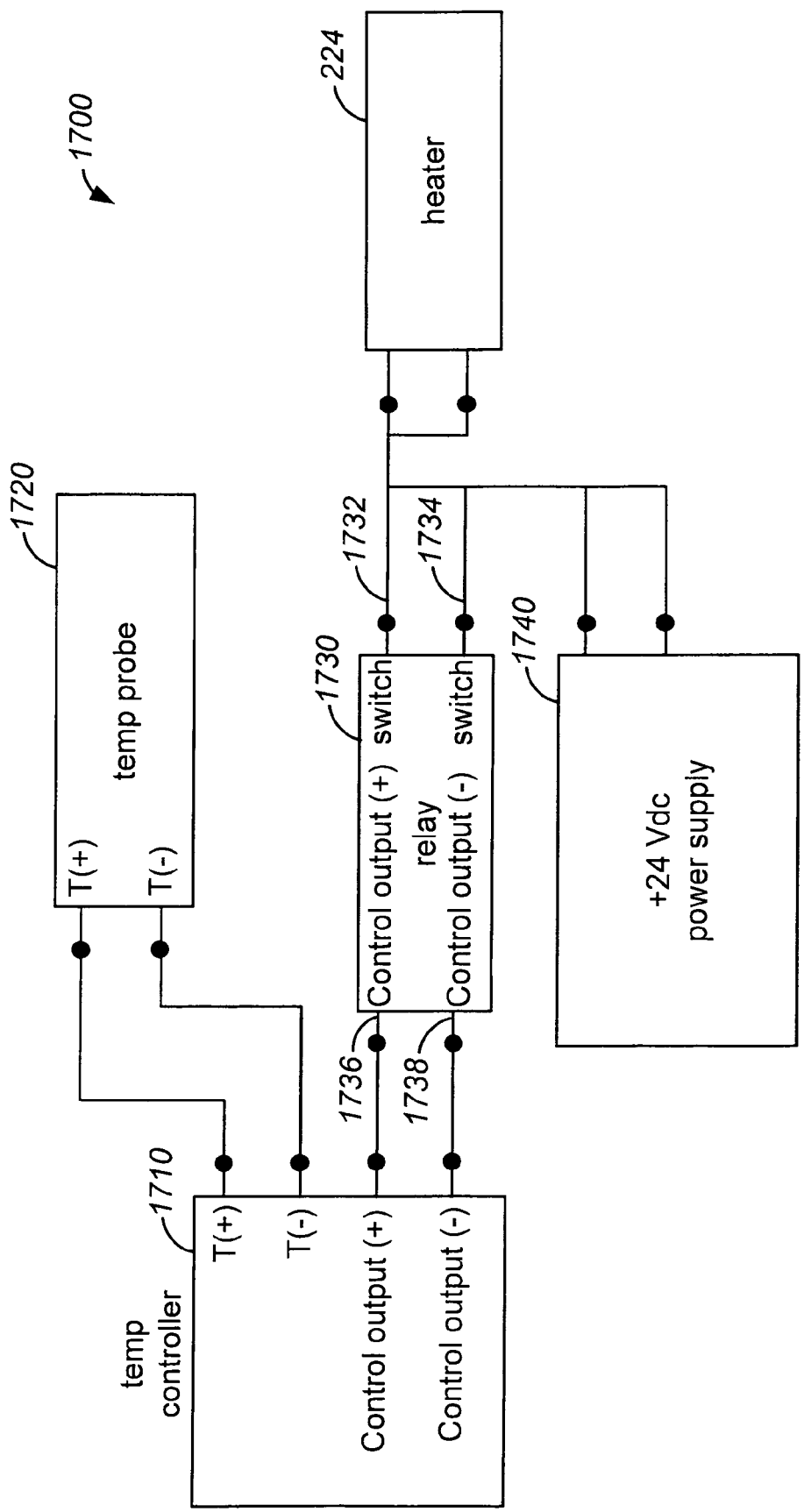
FIG. 17 is a schematic diagram of an embodiment of a heating subsystem.

Referring now to FIG. 16, the procedures represented by the block flow diagrams of FIGS. 10-15 are operated together to automate the data collection. The sequence of events is as follows: (i) the humidity and total flow and concentrations are set in accordance with the procedure represented by the block flow diagram in FIGS. 11-12; (ii) one of the nanotube sensors of the sensor 286 is selected in accordance with the procedure represented by the block flow diagram in FIG. 13; (iii) the gate voltage output waveform is started in accordance with the procedure represented by the block flow diagram in FIG. 14; and (iv) the data is acquired and stored in memory for a pre-determined number of sweeps (e.g. 16 times from −V to +V and back to −V) and then saved to disk, in accordance with the procedure represented by block flow diagram in FIG. 15. The gate voltage output of FIG. 14 is stopped, a new nanotube sensor is selected in accordance with the procedure represented by the block flow diagram in FIG. 13, and data is acquired again in accordance with the procedure represented by block flow diagram in FIG. 15. After all the nanotube sensors are finished sensing, a new concentration is chosen and the process repeated.

Figure 3:
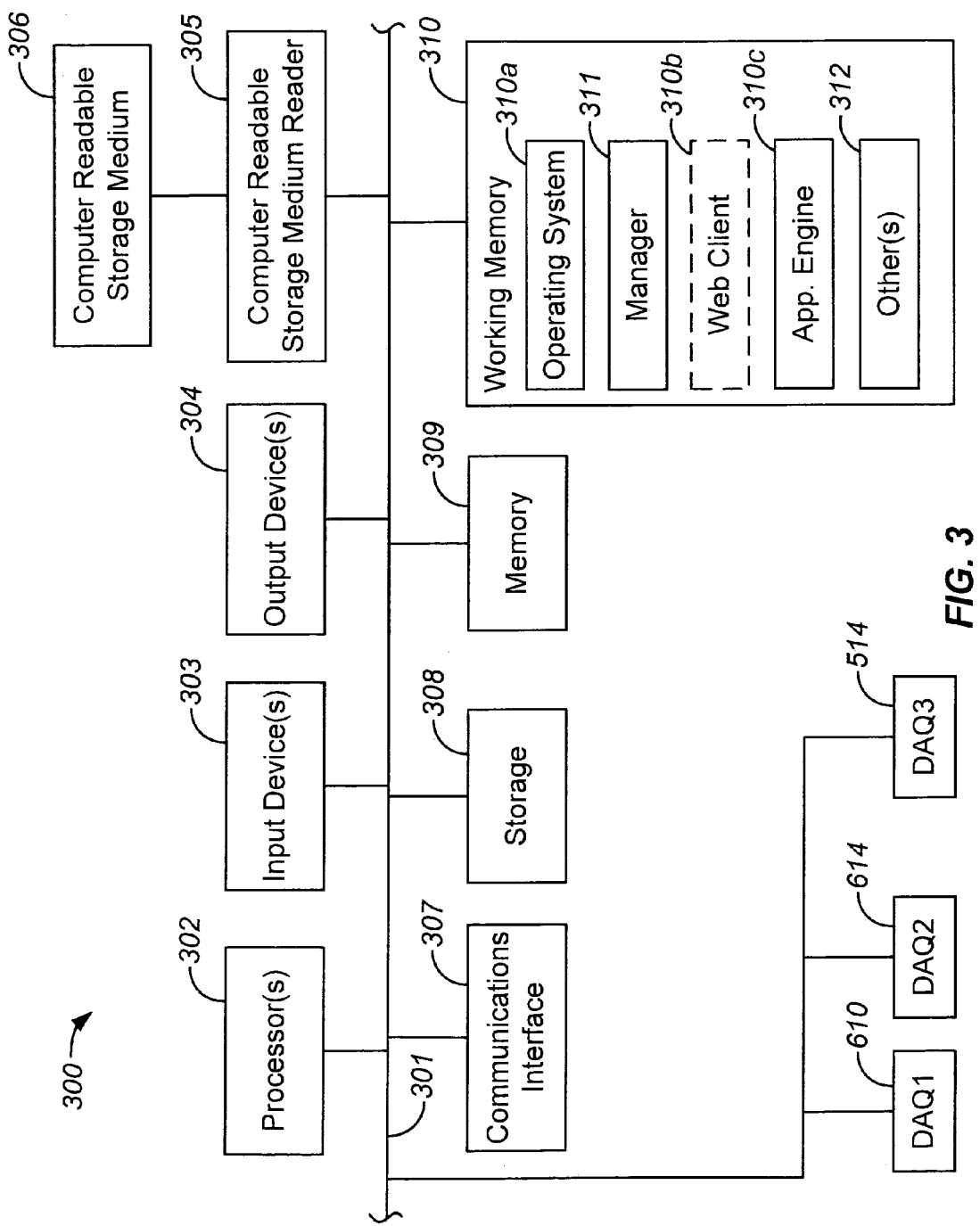
FIG. 3 is a schematic diagram illustrating an exemplary computing system for operating embodiments of the present invention.
Figure 4:
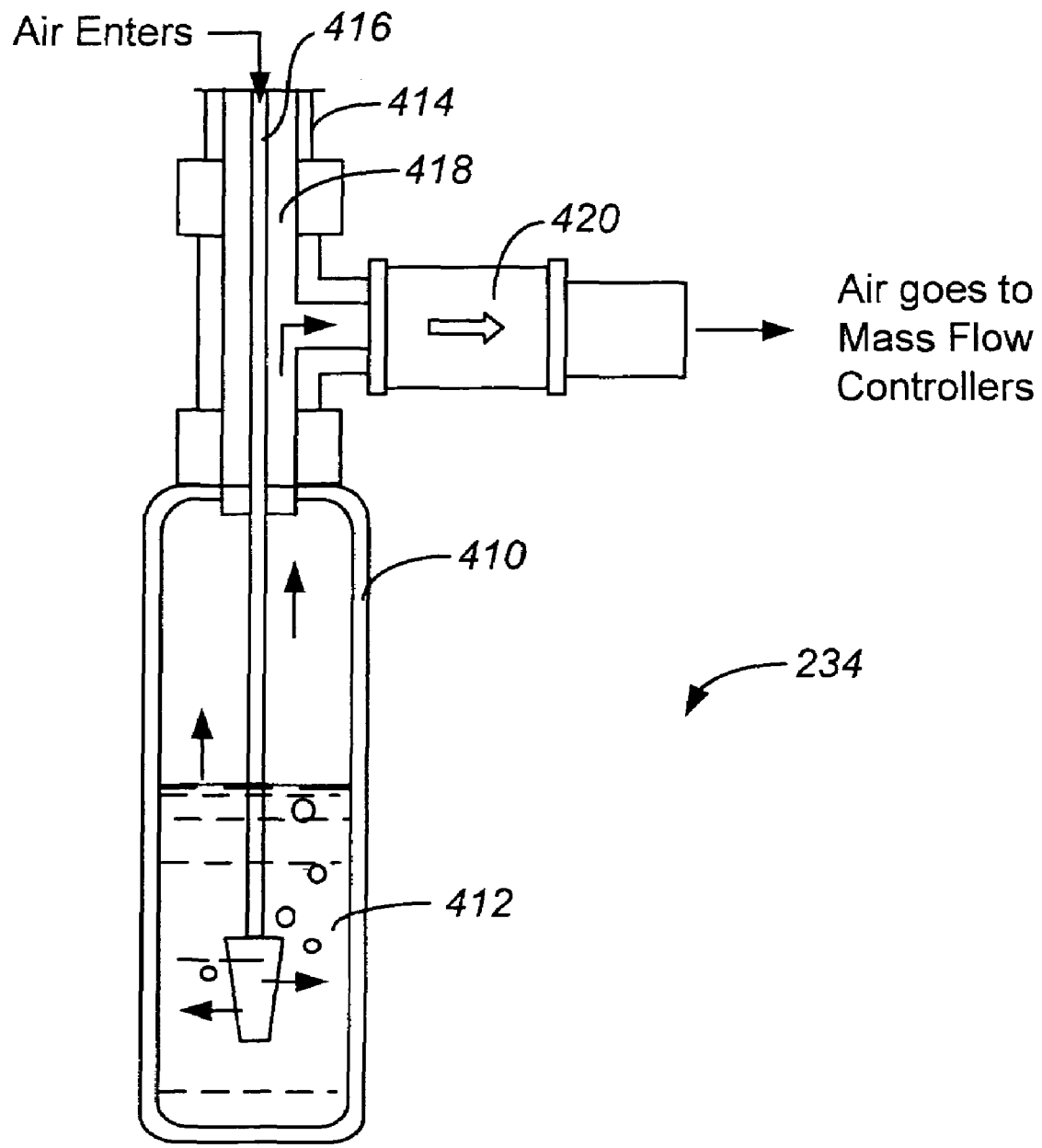
FIG. 4 is a sectional view of a humidifier for humidifying air.

More particularly and continuing to refer to FIG. 16, there is seen a schematic block flow diagram for the software which implements the automation of data collection for embodiments of the present invention utilizing such a computer system 300 of FIG. 3. The block flow diagram in FIG. 16 represents program control structures. Blocks 1610, 1620 and 1630 respectively represent list of desired flow rates, list of desired odor A concentration, and list of desired odor B concentrations. The desired total flow rate to sensor (block 1210, also in FIG. 12), the desired odor A percent to sensor (block 1220, also in FIG. 12), and the desired odor B percent to sensor (block 1224, also in FIG. 12) are chosen from the respective lists represented by blocks 1610, 1620 and 1630. From a list of desired sensors (block 1640), the next sensor is chosen in accordance with block 1310 (the desired sensor number represented by block 1310 in FIG. 13) and this value is sent ("code" of block 1328) to the circuit board 514 (block 1310, DAQ3 in FIG. 5) and on to the analog switches (multiplexers 510 and 512) to select the appropriate sensor in accordance with the procedure represented by the block flow diagram in FIG. 13. After the procedure represented by the block flow diagram of FIG. 13, the procedure represented by the block flow diagram of FIG. 14 operates to turn on the sweeping of the gate voltage vis-à-vis 1644 sent to DAQ3 analog output channel 0 1458, also in FIG. 14. The computer structure executes the operation represented by blocks 1510 and 1550 (also in FIG. 15), more specifically executing to collect the data from the sensor 286 and save it to disk storage (block 1550). Once the predetermined amount of data is acquired, the gate voltage output waveform is stopped ("stop" command of block 1658) in accordance with the procedure represented by FIG. 14, and a stop signal is sent to the circuit board 514 (block 1458, DAQ3 in FIG. 5). Subsequently, the next iteration of sensor selection (block 1310) proceeds (e.g. the next sensor is selected). The program proceeds by iterating through each software structure in turn until all iterations are processed. When the lists of flow rates and concentrations are exhausted, the program ends by turning off all flow to the sensor assembly 216 and through the humidifier system.

Description of Analysis Procedures for Molecule Identification

The molecule identification procedure has two(2) main parts for embodiments of the present invention. The first part is a preliminary building of a molecule database. The second part is the identification of a sampled molecule with respect to the molecule database.

Building a Molecule Database

Software Design

Figure 7:
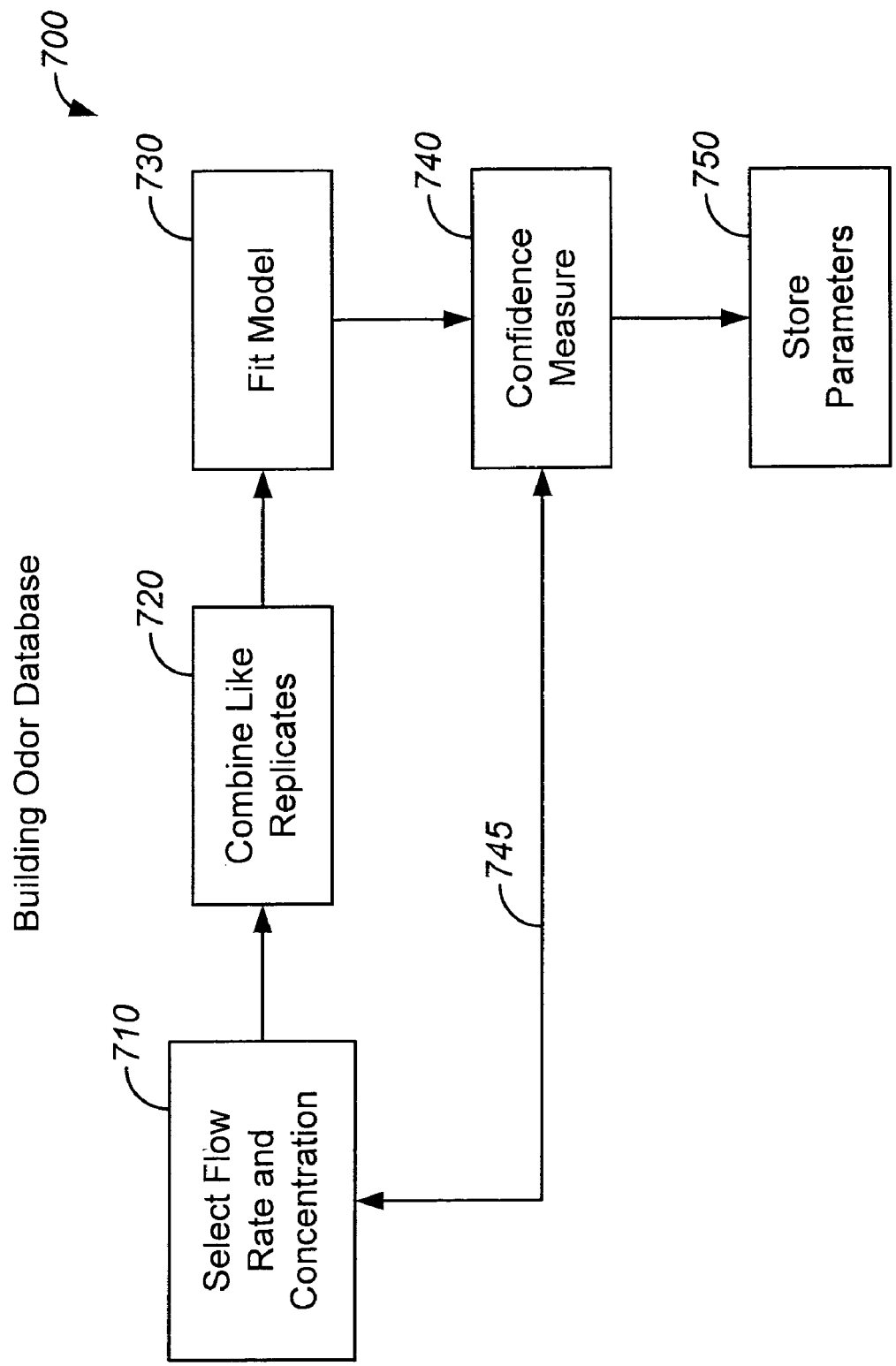
FIG. 7 is a block flow diagram of a procedure for building a molecule data base in accordance with embodiments of the present invention.

FIG. 16 is a schematic block flow diagram for each molecule to be included in the database (e.g. thousands of molecules), which may be stored in storage 308 of the computer system 300 of FIG. 3. First, a mixture of molecule and air is prepared. Then, prespecified flow rates of the mixture of molecule/air are assigned or selected, along with concentrations of molecule in the mixture of molecule/air, as reflected by the instructions in block 710 ("Select Flow Rate & Concentration") of FIG. 7. Each mixture of molecule/air is sampled at each of a prespecified number of flow rates and concentrations. For each such combination of molecule, flow rate and concentration, a number of replicates or identical samples are taken and the output of the sensor 286 is recorded for each replicate. Then, these replicates are averaged together to produce an average response profile for the given molecule at the given concentration and flow rate, as reflected by the instructions in block 720 ("Combine Like Replicates"). This average response profile is then fit to a mathematical model, e.g. a polynomial curve using a least-squares or Levenberg-Marquardt simplex minimization procedure, as reflected by the instructions in block 730 ("Fit Model"). In accordance with the instructions in block 740 ("Confidence Measure"), an error term or confidence measure is also computed. This is done by fitting each individual replicate to the same parametric model so that for each parameter we have a set of estimates. For example, the sum of the variance of each replicate parameter estimate from the value of the mean of the sample reflects the uncertainty in any estimate of the parameters and is a confidence measure. If this number is less than a prespecified threshold (e.g., +or −3%), then the average response profile and its associated parameters are accepted. If it is above the threshold, additional replicates should be collected, as indicated by bi-directional arrow 745 in FIG. 7. This process continues until the confidence threshold is met. [This procedure is a simple confidence measure, and more complicated versions involving weighting some of the parameters more than others, using the variance of the residuals from the fit as a measure of confidence, etc. are also possible, and are within the spirit and scope of embodiments of the present invention]

Once an average response profile with acceptable confidence measure is obtained, the parameter values, as well as the number of replicates required and the variance of each parameter, are stored in the database for that molecule and flow rate and concentration combination, in accordance with the instructions of block 750 ("Store Parameters"). Then this procedure is applied to the next molecule and flow rate and concentration procedure. Subsequently, this procedure is continued until a large data base of molecules is produced, forming the basis for identifying any unknown substance or molecule in accordance with embodiments of the present invention. Once a database is formed, a data trimming procedure may be applied if one suspects that equipment or procedural irregularities may have distorted some the data collected. This may be done by either trimming outliers from the fitted parameter distributions for each molecule at each flow rate or concentration (e.g., trimming out the most extreme 5% of the samples and replacing them with new samples) or by trimming out those samples that had the largest residual variance from the mean polynomial fit for a given molecule at a given flow rate and concentration. Any appropriate data trimming procedure may be applied.

Molecule Identification Procedure

Figure 8:
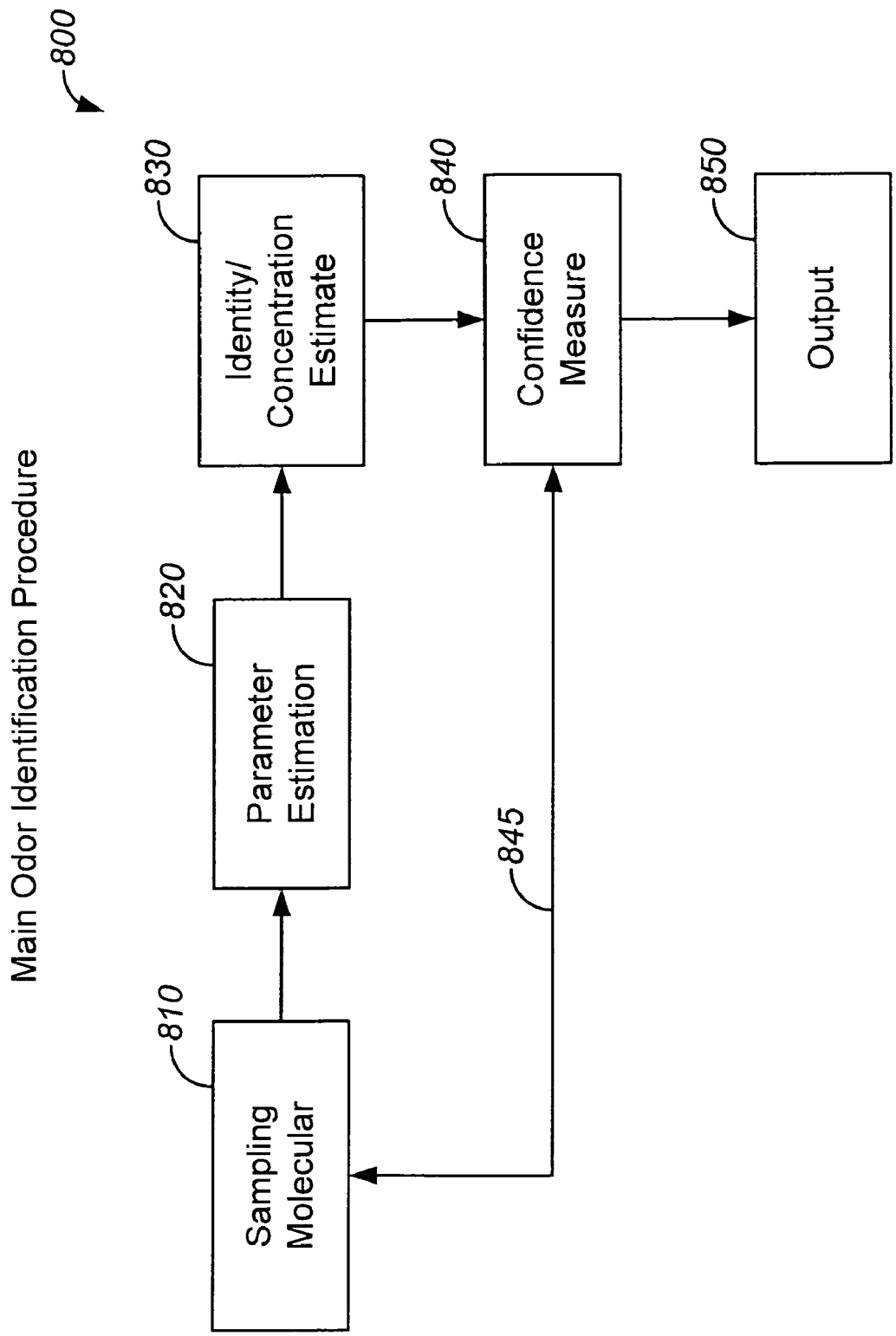
FIG. 8 is a block flow diagram of a procedure for broadly identifying one or more particles (e.g., molecules) of a substance in accordance with embodiments of the present invention.

Referring now to FIG. 8 there is seen an embodiment of the molecule identification procedure, generally shown as 800 in FIG. 8. An unknown molecule at an unknown concentration is sampled (preferably simultaneously) at a number of different flow rates in accordance with the instructions of block 810 ("Molecular Sampling"). For each sample (at each flow rate) the response of the sensor 286 is fit to a mathematical model (specified in the molecule database) so that the parameters of the model are derived, as reflected by the instructions in block 820 ("Parameter Estimation"). These parameters are then compared to the database which returns the best matching molecule and concentration, as reflected by the instructions in block 830 ("Identity/Concentration Estimate"), and the confidence with which the match is made, as reflected by the instructions in block 840 ("Confidence Measure"). If the confidence is greater than a prespecified threshold, the match is accepted and produced as output in accordance with the instructions of block 850 ("output"). If it is not greater, additional samples are required and taken, as indicated by bi-directional arrow 845 in FIG. 8. These additional samples may be replicates of the existing flow rates which are then averaged with the previous samples. These additional samples may also be new samples at additional flow rates if all flow rates have not already been sampled.

In the case of mixtures of 2 or more kinds of molecules, the results of the matching procedure may either show a split response to the two different molecules, i.e. the different information from different flow rates may support one or the other molecular identification, or the response of the mixture may match erroneously to a third molecule. The use of a larger number of flow rates for each sensor, and a larger number of sensors for each flow rate, will tend to reduce the number of erroneous matches and increase confidence in the split responses indicating the presence of more than one molecule. It is understood, that the foregoing discussion refers to molecules beyond those that are always present in the carrier medium, e.g. oxygen, nitrogen, carbon dioxide, in the case of air as a carrier medium. It is also understood that these molecules (oxygen, nitrogen, carbon dioxide, etc) could be the molecules for which a signature is being collected. In these cases, and for other gases (e.g. hydrogen, or any other substance that is in gas phase at the desired temperature), a different embodiment of the apparatus would be used. In this embodiment a pure gas (e.g. carbon dioxide) could be mixed with breathing air to provide different concentrations to the sensor.

Details of Database Comparison

Figure 9:
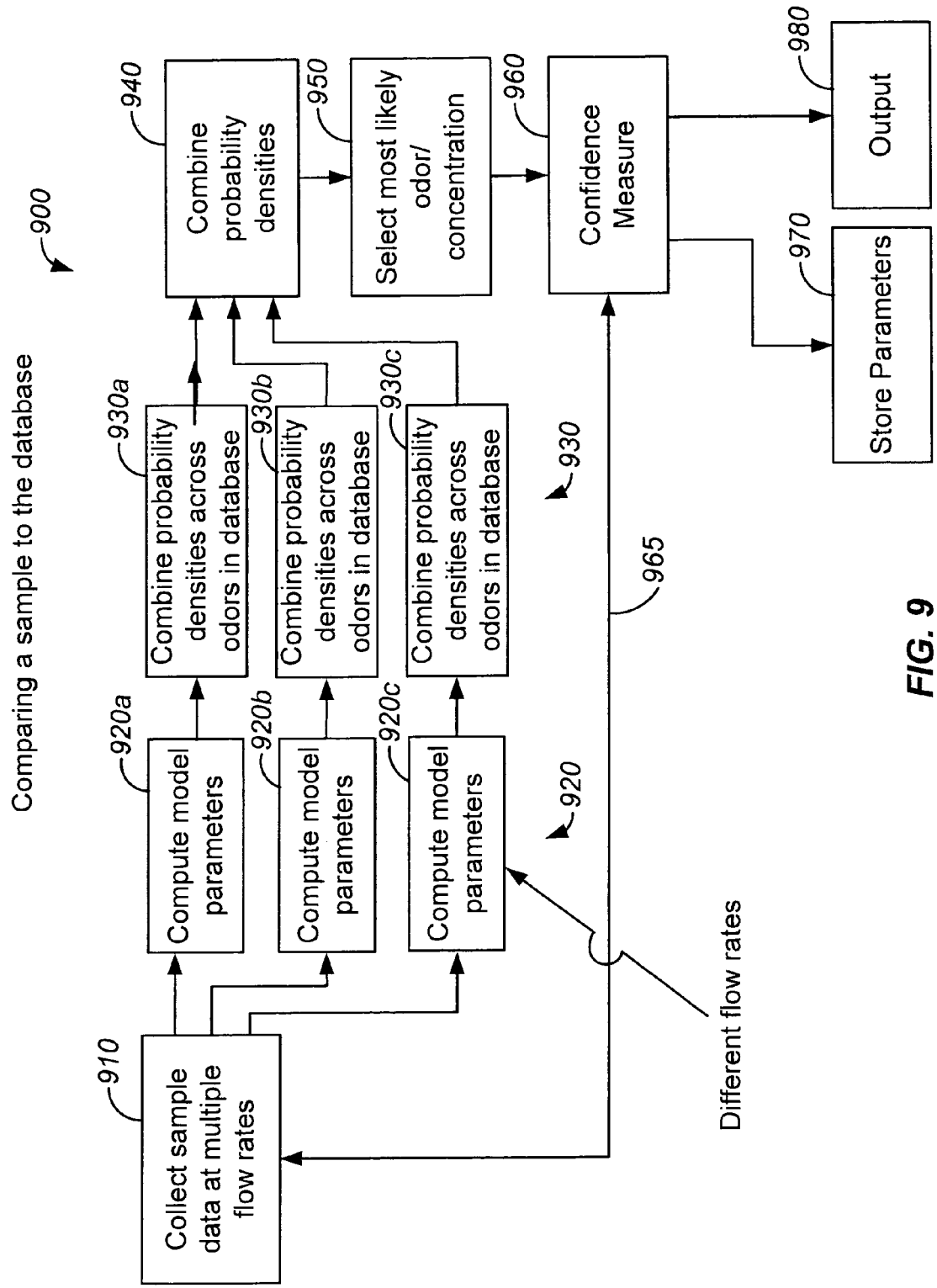
FIG. 9 is a block flow diagram of a procedure for more specifically identifying one or more particles (e.g., molecules) of a substance in accordance with embodiments of the present invention.

The details of the database comparison procedure in accordance with embodiments of the invention are shown in FIG. 9. Samples of an unknown molecule in air are taken at a number of different flow rates as indicated by the instructions of block 910 ("Collect Sample Data at Multiple Flow Rates"). Multiple samples at each flow rate may be taken at each flow rate and averaged together for greater reliability. For each flow rate, model parameters are computed, as broadly illustrated as 920 in FIG. 9, or as more specifically illustrated by the instructions in blocks 920a, 920b, and 920c ("Compute Model Parameters) for each of the (three) flow rates. The sensor response to each flow rate is fit to a parametric model. Thus, the input to the database lookup is a set of parameters (representing the sensor response) at each of a series of different flow rates. As previously indicated, the database consists of information for a large set of molecules sampled at known concentrations and flow rates. To find a match, the following is done:

For each flow rate, for each entry in the database at the given flow rate, a probability, as broadly illustrated as 920 in FIG. 9, or as more specifically illustrated by the instructions in blocks 920a, 920b, and 920c ("Combine Probability Densities Across Molecules in Database") for each of the (three) flow rates, that the current sample belongs to the population that produced the entry is computed (using the mean and variance information stored in the database for each entry). For each flow rate, model parameters are computed, Thus, for each flow rate there is a probability distribution over molecules and concentrations in the database. In accordance with the instructions in block 940 ("Combine Probability Densities"), these distributions across flow rates are then combined (for example, added or multiplied) into a "likelihood index" so that an overall distribution across molecules and concentrations combining information from the different flow rates. It is to be understood that whereas these formulations may be done with probability distributions and likelihood values, the procedure is not limited to such formulations and can be done with any functions that define a distance or distribution over the parameter space. Indeed an equivalent formulation with distances, using for example Mahalanobis distance within the parameter space as a distance metric is essentially equivalent to the approach using probability distributions and provides essentially the same results.

In accordance with the instructions in block 950 ("Select Most Likely Molecule/Concentration"), the most likely molecule/concentration value for the sample is selected. Therefore, the molecule (i.e., molecule(s)) and concentration value that has the highest "likelihood index" is the most likely given the information from the different flow rates. This is the candidate match, and would be produced as output in accordance with the instructions of block 980 ("Output").

A confidence measure, as indicated by block 960 ("Confidence Measure"), for this candidate match is computed by measuring the degree of agreement across the multiple samples at different flow rates, e.g. by taking the sum of the squared error across the probability distributions with respect to the likelihood index distribution. Any other statistic that describes agreement across replicates may also be used, e.g. variance of residuals from a fit, trimmed variance measures, etc.

If the confidence for the candidate match exceeds a pre-specified threshold, then it is returned to the user as a match for the current molecule, per instructions of block 980. If it does not, then more data samples are collected and the entire procedure repeated in accordance with bi-directional arrow 965 in FIG. 9. The sampled data (or the parameters for the fitted samples) may also be stored in the database (e.g., storage 308 in FIG. 3) to be incorporated into and augment future versions of the database, all as reflected by the instructions in block 970 ("Store Parameters").

It is to be understood that with respect to "Fitting to the Parametric Model," the fitting of data to a model is highly desirable as it reduces noise. However, one could in fact not apply a parametric model and do comparisons entirely in the raw input space. This would make the comparison noisier, and is feasible given a sufficiently smooth response space. It is also to be understood that the spirit and scope of the present invention includes a null model for various embodiments of the present invention.

It should be understood that the present embodiment of the system and method for preparing and delivering molecules at two or more flow rates to a sensor is only for illustrative purposes. Other ways and means for preparing and delivering molecules are within the spirit and scope of the present invention. For example, instead of positive pressure at reservoir 11 there could be atmospheric pressure with a vacuum appropriately disposed (e.g., at the end point or opposite side of sensor assembly 286). By further way of example, is a 'jet-assisted' technique. Molecules are often embedded in a material (say a persons clothing) and one can use pressurized air (a 'jet') to force out the molecules and then these molecules are picked up by a vacuum and then directed to the sensor assembly 286.

Embodiments of the present invention will be illustrated by the following set forth examples which are being given to set forth the presently known best mode and by way of illustration only and not by way of any limitation. It is to be understood that certain materials, chemical compositions and conventional procedures referred to below, but not explained, are well documented in published literature and known to those artisans possessing skill in the art. All materials and chemical compositions whose source(s) are not stated below are readily available from commercial suppliers, who are also known to those artisans possessing skill in the art. All parameters such as concentrations, mixing proportions, temperatures, rates, compounds, etc., submitted in these examples are not to be construed to unduly limit the scope of the invention.

EXAMPLE

As a means of assessing the performance of the sensors individually and in combination, we have collected data using the described apparatus and analyzed the data using the described algorithms. We tested a set of 26 molecules at each of 4 flow rates and 5 concentrations with 11 sensors. We detail a method using which we were able to exceed about 99% correct classification of molecules and concentration.

Apparatus Setup

The previously described apparatus for various embodiments of the invention allows for the controlled delivery of a stimulus to a particular sensor. Additionally, there is control circuitry and amplification associated with the sensor that allows measurement of the sensor. The sensor measurements were recorded by the software and then stored on disk. The stored data was then analyzed, as described previously, to estimate the prediction accuracy of the data collected.

Data was collected with 2 ml of liquid molecule in each of two hex-head caps of molecule canisters. We used the following molecules or substances:

1-Octen-3-ol
4-Heptanone
Acetone
Acetophenone
Amyl_Acetate
Benzaldehyde
Benzene
Decyl_aldehyde
Dodecane
Dodecyl_aldehyde
Ethyl_alcohol
Ethyl_heptanoate
Eugenol
Geranioil
L-Carvone
Limonene
Nonane
Nonyl_aldehyde
Octyl_aldehyde
Phenethyl_alcohol
Propionic_acid
R-Carvone
Toluene
Undecyclic_aldehyde
Valeric_acid
Water After all of the molecules were admixed and a first sample was loaded into the hex-head caps of molecule canisters of the apparatus, the LabView software was started to generate the stimulus and acquire the data. The LabVIEW software controlled humidity to 55% (room humidity) and temperature was controlled to 22° C. The software directed the apparatus to deliver air to the sensor at 6, 9, 12, and 15 LPM. Also, the software controlled the ratio of odorized air to dilution air to be 0% molecule (e.g. all dilution air), 25% molecule (75% dilution), 50% molecule (50% dilution), 75% molecule (25% dilution), or 100% molecule (no dilution). The LabVIEW software collected 16 sweeps of the gate voltage from −5V to +5V. Once the 16 sweeps were acquired, the LabView software stopped the stimulus delivery. The hex-head caps of molecule canisters containing the molecules were removed from the apparatus. The next or second sample of the molecules was measured (2 ml per cap) and two caps were placed in the apparatus and the data collection process started anew. When all data was collected for this experiment, 8320 sweeps were collected (26×4×5'16=8320; 26 molecules each at 4 flow rates, 5 concentrations with 16 replicates of each combination). These data was used by the analysis procedure previously described.

Data Analysis

The analysis consisted of 2 parts. The first part consisted of characterizing the sensor response to each of the trials (a particular run of a molecule to be identified at a particular concentration and flow rate) and the compilation of this information into a database. The second part consisted of testing a single trial against the database to determine whether there was a correct match. Data were collected for each of 11 sensors, each of which had slight variations in. We tested 26 molecules, each at 4 flow rates and 5 concentrations with 16 replicates for each combination.

Figure 22:
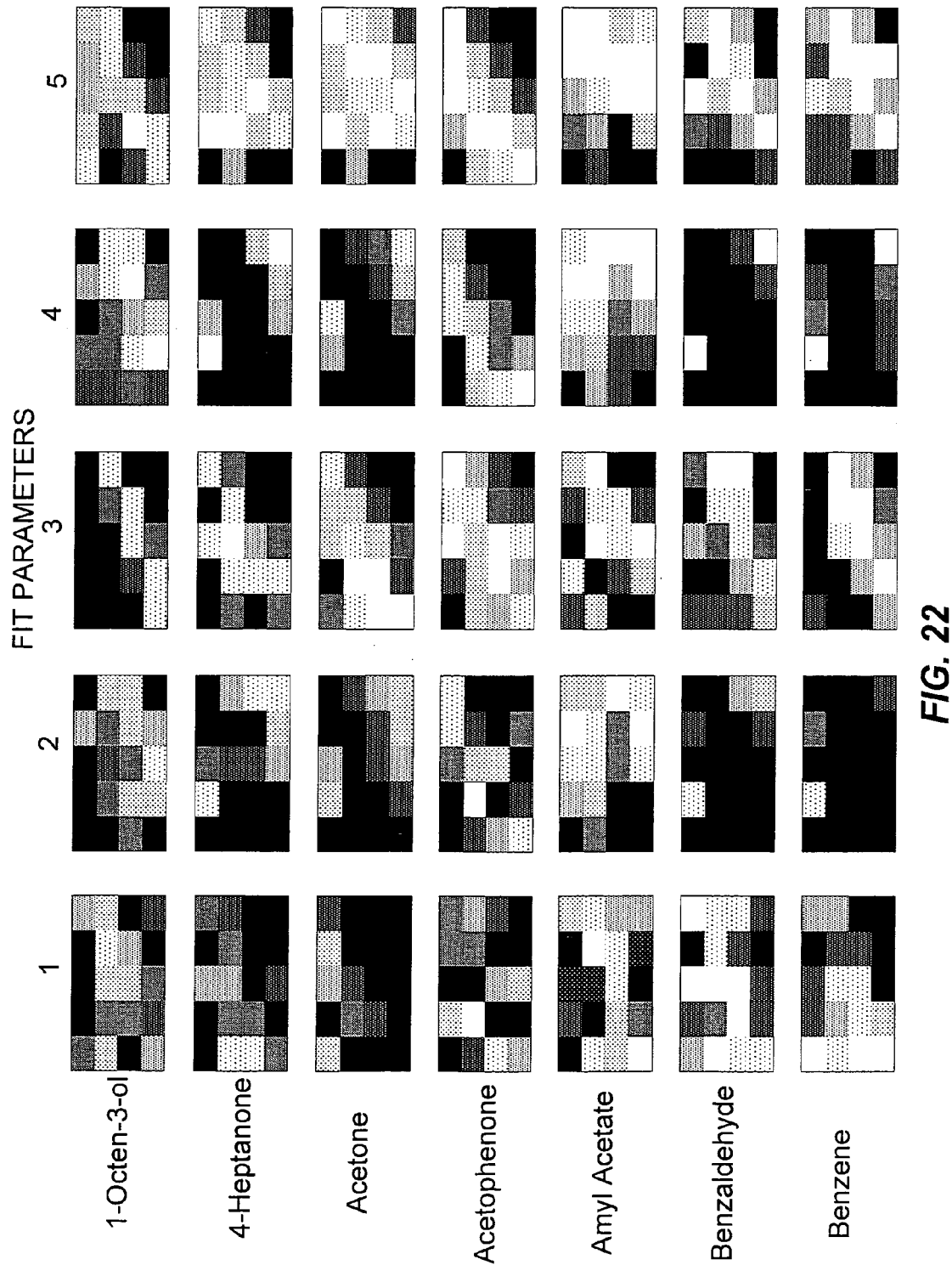
FIG. 22 is a color schematic representing fit parameters for 7 molecules of the Example.

Each trial (a single exposure of a molecule to a single sensor) was fit with a 4 degree (5 parameter) polynomial using least squared error. Examples of the sensor response and its corresponding fitted polynomial for 2 molecules (i.e., acetone and benzene) at each of 2 concentrations and flow rates are shown in FIGS. 18-21. The change in sensor response at different flow rates and concentrations is clearly seen for each of the 2 molecules, acetone and benzene. It should also be observed that the 4-degree polynomial provides an excellent fit to the data. Perforce, higher degree polynomials will provide marginally better fits, but they have the disadvantages of reducing the data to a higher dimensional space and may in fact over fit the data, i.e. model too much noise as well as data. The trade-off between the advantages of a low dimensional fitting space that may under fit the data, and a high dimensional space that may over fit it, is a common problem in data modeling in general, and but we found however that a range of polynomial fits provided similar results. FIG. 22 shows a graphical representation of the parameter space obtained for a sample of 7 molecules. In FIG. 22, each of the 7 rows corresponds to a particular molecule (as labeled in the figure) and each column corresponds to each of the 5 parameters of the 4-degree polynomial fit. Each sub panel of 20 colored squares (4 by 5) represents the value (on a color scale) of that parameter for each combination of molecule flow rate (rows) and concentrations (columns). Thus, the first row represents the 5 parameters for 1-octen-3-ol. Within the block representing the first parameter, each of the four rows corresponds to increasing flow rates (6, 9, 12 and 15 liters/minute, top to bottom) and each of the five columns represents increasing concentrations of the substance (left to right, 0%, 25%, 50%, 75% and 100% dilution in air).

Once all the data has been collected and stored, a cross-validation procedure was used to assess the identification performance of the system. Each single trial was assessed by excluding it from the database (so that its set of replicates was reduced to 15 rather than 16) and then running a matching procedure on it against the database and recording whether it was correctly matched or not. For example, one of the trials for acetone at flow rate 1 and concentration 1 will be withdrawn from the database, and then it will be matched against the database. If the acetone trial is identified as acetone rather than some other molecule in the database, this is counted as a success. If it is matched to some other molecule, this is a miss. If it fails to match to any molecule with sufficiently high confidence, this is a failed trial. By applying this cross-validation procedure successively to each trial in the database, we can estimate the overall numbers of successes, misses and failures and thus characterize the performance of the system.

In addition, because the database contains information about both molecular and concentration, the processing for molecular matching also contains a molecular concentration match. Thus, we can also assess the performance of the system for matching molecular concentration, as well as identity.

Figure 23:
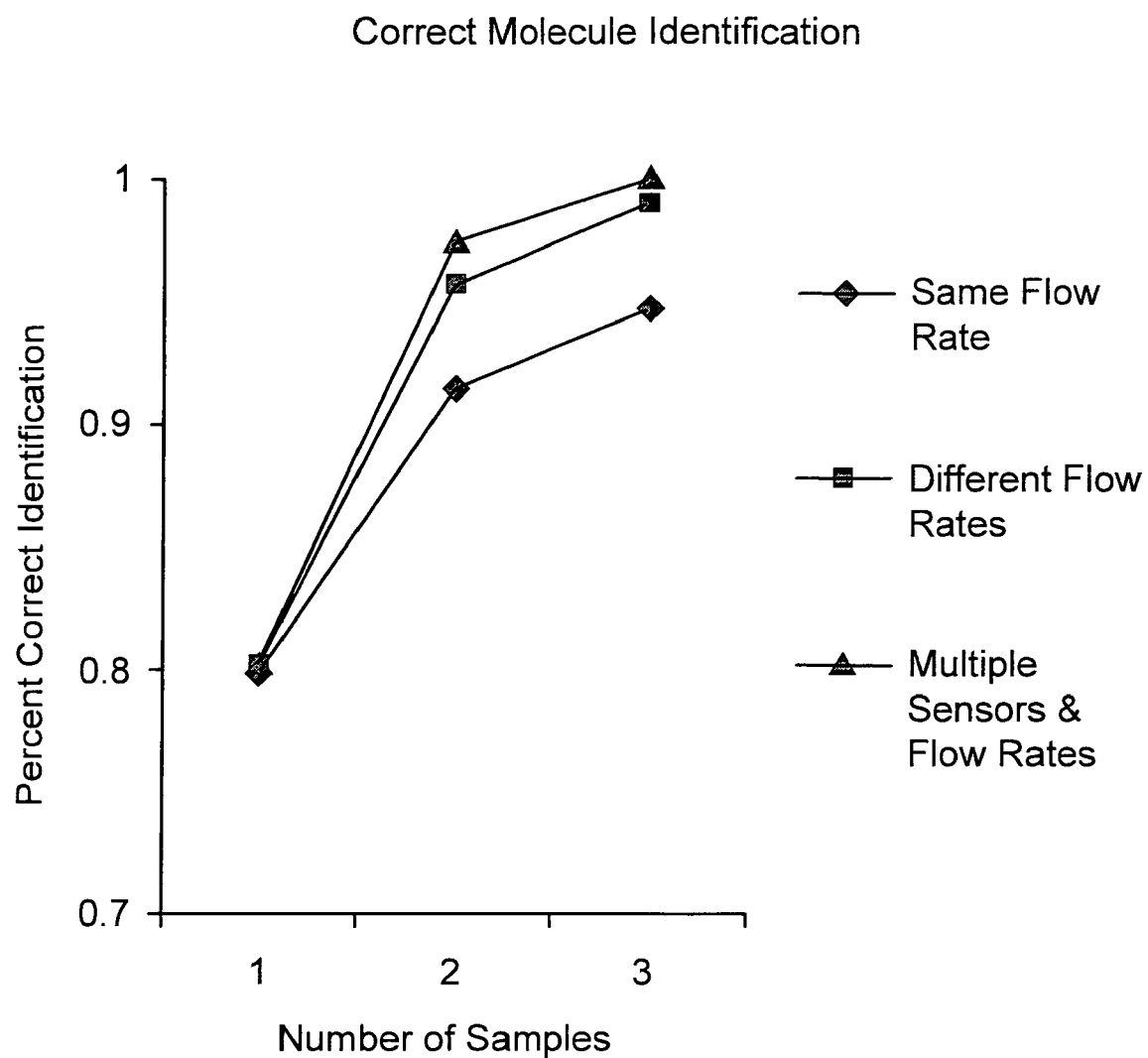
FIG. 23 illustrates the performance of a molecule-identifying system as described in the Example.

FIG. 23 illustrates the performance of the system in a typical setup. The procedure used to identify a match was as follows. For each condition (a particular molecule at a particular flow rate and concentration) the parameters of the 4-degree polynomial fit placed each sample in a 5 dimensional parameter space. Thus, given we had 16 trials per condition, we had 16 points in a five dimensional space. This space was modeled as a multivariate normal space, so that the covariance matrix determined the structure of the space. The degree of membership of a given point in this 5 dimensional space was modeled as the inverse of Mahalanobis distance with respect to the covariance matrix derived from the condition. The confidence with which a match is made was defined as a minimum distance threshold. Thus, the system identifies a candidate trial as belonging to the condition in its database with the minimal distance, provided that at least 1 condition exceeded the minimal distance specified by the confidence threshold. If no condition satisfies this threshold, then a failure to match is returned. When multiple flow rate trials are to be combined, the individual Mahalanobis distances for each trial are summed together so that the distances for a given condition is the sum of the distances for each trial. The rest of the procedure is identical to the single trial case.

Results using a confidence threshold of Mahalanobis distance <5 (Mahalanobis distance is standardized distance in the parameter space assuming a multivariate normal distribution of samples), are shown in FIG. 23. The three graphs (i.e., the blue, green and red curves) in FIG. 23 shows percentage correct molecule identification combining each of 1, 2, or 3 trials of data. As can be seen, combining multiple trials of the same condition increases performance, as is expected from the decreased noise in combining like trials (blue curve). However, a key point is that combining information across trials having different flow rates of the same molecule type and concentration significantly improves results (green curve). In other words, the information obtained from sampling at different flow rates significantly exceeds the information increase in resampling at the same flow rate. Finally, combining information across different sensors (red curve) and different flow rates, further increases the performance of the system. This indicates that the different sensors in fact responded differentially to the different molecules.

The results showed that, we were not only able to identify the molecular identity with over 99% accuracy, we were able to identify the molecular concentration as well in almost all cases. In addition when molecular identity was established, the correct molecular concentration was identified in over 98% of cases. In other words, treating individual concentration levels of the same molecule as different categories, our matching procedure was able to produce over 99% performance within these subcategories.

CONCLUSION

In the description herein for embodiments of the present invention, numerous specific details are provided, such as examples of components and/or methods, to provide a thorough understanding of the embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Any suitable programming language can be used to implement the routines of the present invention including C, C++, Java, assembly language, etc. Different programming techniques such as procedural or object oriented can be employed. The routines can execute on a single processing device or multiple processors. Although the steps, operations, or computations may be presented in a specific order, this order may be changed in different embodiments. In some embodiments, multiple steps shown sequentially in this specification can be performed at the same time. The sequence of operations described herein can be interrupted, suspended, or otherwise controlled by another process, such as an operating system, kernel, etc. The routines can operate in an operating system environment or as stand-alone routines occupying all, or a substantial part, of the system processing.

In the description herein for embodiments of the present invention, a portion of the disclosure recited in the specification may contain material which is subject to copyright protection. Computer program source code, object code, instructions, text, or other functional information that is executable by a machine may be included in an appendix, tables, figures, or in other forms. The copyright owner has no objection to the facsimile reproduction of the specification as filed in the Patent and Trademark Office. Otherwise all copyright rights are reserved.

A 'computer' for purposes of embodiments of the present invention may include any processor-containing device, such as a mainframe computer, personal computer, laptop, notebook, microcomputer, server, personal data manager or 'PIM' (also referred to as a personal information manager), smart cellular or other phone, smart card, set-top box, or any of the like. A 'computer program' may include any suitable locally or remotely executable program or sequence of coded instructions, which are to be inserted into a computer, well known to those skilled in the art. Stated more specifically, a computer program includes an organized list of instructions that, when executed, causes the computer to behave in a predetermined manner. A computer program contains a list of ingredients (called variables) and a list of directions (called statements) that tell the computer what to do with the variables. The variables may represent numeric data, text, audio, or graphical images. If a computer is employed for assisting in operating any of the assemblies or for conducting any of the procedures described herein, the computer would have suitable instructions (e.g., source code) for allowing the assemblies to be operated, or the procedures to be conducted, as such in accordance with embodiments of the present invention. Similarly, if a computer is employed for presenting any data or media via a suitable directly/indirectly coupled input/output (I/O) device, the computer would have suitable instructions for allowing a user to input or output (e.g., present) program code and/or data information, respectively in accordance with the embodiments of the present invention.

A 'computer readable medium' for purposes of embodiments of the present invention may be any medium that can contain, store, communicate, propagate, or transport the computer program for use by or in connection with the instruction execution system apparatus, system, or device. The computer readable medium can be, by way of example only but not by limitation, an electronic, magnetic, optical, electromagnetic, infrared, or semiconductor system, apparatus, system, device, propagation medium, or computer memory. The computer readable medium may have suitable instructions for assisting in operating any of the assemblies or for conducting any of the procedures described herein, or for providing for input or presenting in accordance with various embodiments of the present invention.

Reference throughout this specification to 'one embodiment', 'an embodiment', or 'a specific embodiment' means that a particular feature, structure, or characteristic described in connection with the embodiment is included in at least one embodiment of the present invention and not necessarily in all embodiments. Thus, respective appearances of the phrases 'in one embodiment', 'in an embodiment', or 'in a specific embodiment' in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as a part of the spirit and scope of the present invention.

Further, at least some of the components of an embodiment of the invention may be implemented by using a programmed general purpose digital computer, by using application-specific integrated circuits, programmable logic devices, or field-programmable gate arrays, or by using a network of interconnected components and circuits. Connections may be wired, wireless, by modem, and the like.

It will also be appreciated that one or more of the elements depicted in the drawings/figures can be implemented in a more separated or integrated manner, or even removed or rendered as inoperable in certain cases, as is useful in accordance with a particular application. It is also within the spirit and scope of the present invention to implement a program or code that can be stored in a machine-readable medium to allow a computer to perform any of the methods described above.

Additionally, any signal arrows in the drawings/figures should be considered only as exemplary, and not limiting, unless otherwise specifically noted. Furthermore, the term 'or' as used herein is generally intended to mean 'and/or', unless otherwise indicated. Combinations of components or steps will also be considered as being noted, where terminology is foreseen as rendering the ability to separate or combine is unclear.

As used in the description herein and throughout the claims that follow, 'a', 'an', and 'the' include plural references, unless the context clearly dictates otherwise. Also, as used in the description herein and throughout the claims that follow, the meaning of 'in' includes 'in' and 'on', unless the context clearly dictates otherwise.

In the description herein for embodiments of the present invention, a portion of the disclosure recited in the specification contains material, which is subject to copyright protection. Computer program source code, object code, instructions, text or other functional information that is executable by a machine may be included in an appendix, tables, figures or in other forms. The copyright owner has no objection to the facsimile reproduction of the specification as filed in the Patent and Trademark Office. Otherwise all copyright rights are reserved.

Exemplary Source Code for the Software

```
% This software implements a method for the creation of
% a molecular information database and a method for
analyzing
% sensor response to molecular exposure so that molecular
% identity may be established. All material is copyright,
% all rights reserved Copyright 2005 The Regents of the
% University of California.
%
% This code takes as input a database created by the code
% in createDataBase.m and does a cross-validation
experiment
% to assess molecular identification performance.
%%%%%%%%%%%%%%%%%%%%%%%%%%%%%%%%%%%%%
% load up the database file:
dataFile=input ('Path to database file: ','s');
load(dataFile) ;
%%%%%%%%%%%%%%%%%%%%%%%%%%%%%%%%%%%%%
% for comparison, pick a single sensor and multiple
% flow rates:
numFlows=nFlows;
numConcs=nConcs;
numReps=nReps;
matchingConfidence=5;        % maximum distance for correct match
(a
                             % confidence measure)
for s=1:numSensors
    disp(['Processing Sensor ',num2str(s)]);
nTrials=0;
odorCorrect=0;
concCorrect=0;
bothCorrect=0;
odorCorrect2=0;
concCorrect2=0;
bothCorrect2=0;
odorCorrect3=0;
concCorrect3=0;
bothCorrect3=0;
for o=1:length(odorData)
    for f=1:numFlows
        for c=1:numConcs
            for r=1:numReps
                dataTrace=squeeze(fitData(o,s,f,c,r,:));
                % now grab the data from a second flow:
                t=0;
                while t==0
                    f2=ceil(rand*numFlows);
                    ri=ceil(rand*numReps);
                    dataTrace2=squeeze(fitData(o,s,f2,c,ri,:));
                    if isfinite(nansum(dataTrace2))
                        t=1;
                    end
                end
                % now grab the data from a third random flow:
                t=0;
                while t==0
                    f3=ceil(rand*numFlows);
                    ri=ceil(rand*numReps);
                    dataTrace3=squeeze(fitData(o,s,f3,c,ri,:));
                    if isfinite(nansum(dataTrace3))
                        t=1;
```

-continued

Exemplary Source Code for the Software

```
                    end
                end
                if ((~isnan(dataTrace)) & (~isnan(dataTrace2)) &
~(isnan(dataTrace3)))
                    % now go through and compute the mahalanobis
distances:
                    for oi=1:numOdors
                        for ci=1:numConcs
mD1(oi,ci)=mahal(dataTrace',squeeze(fitData(oi,s,f,ci,:,:))
);
mD2(oi,ci)=mahal(dataTrace2',squeeze(fitData(oi,s,f2,ci,:,:
)));
mD3(oi,ci)=mahal(dataTrace3',squeeze(fitData(oi,s,f3,ci,:,:
)));
                        end
                    end
                    % standardize the distributions:
                    mD1=mD1/median(mD1(:));
                    mD2=mD3/median(mD2(:));
                    mD3=mD3/median(mD3(:));
                    % with 1 flow rate:
                    mD=mD1;
                    ii=find(mD==min(mD(:)));
                    if(min(mD(:))<matchingConfidence)
                        guess=indices2Coords(ii,size(mD));
                    else
                        guess=[0 0];
                    end
                    if guess(1)==o
                        odorCorrect=odorCorrect+1;
                    end
                    if guess(2)==c
                        concCorrect=odorCorrect+1;
                    end
                    if ((guess(1)==o) & (guess(2)==c))
                        bothCorrect=bothCorrect+1;
                    end
                    % with 2 flow rates:
                    mD=(mD1+mD2)/2;
                    ii=find(mD==min(mD(:)));
                    if (min(mD(:))<matchingConfidence)
                        guess=indices2Coords(ii,size(mD));
                    else
                        guess=[0 0];
                    end
                    if guess(1)==o
                        odorCorrect2=odorCorrect2+1;
                    end
                    if guess(2)==c
                        concCorrect2=odorCorrect2+1;
                    end
                    if ((guess(1)==o) & (guess(2)==c))
                        bothCorrect2=bothCorrect2+1;
                    end
                    % with 3 flowrates:
                    mD=(mD1+mD2+mD3)/3;
                    ii=find(mD==min(mD(:)));
                    if (min(mD(:))<matchingConfidence)
                        guess=indices2Coords(ii,size(mD));
                    else
                        guess=[0 0];
                    end
                    if guess(1)==o
                        odorCorrect3=odorCorrect3+1;
                    end
                    if guess(2)==c
                        concCorrect3=odorCorrect3+1;
                    end
                    if ((guess(1)==o) & (guess(2)==c))
                        bothCorrect3=bothCorrect3+1;
                    end
                    nTrials=nTrials+1;
                end % NaN check
            end %r
        end %c
    end %f
end %o
```

-continued

Exemplary Source Code for the Software

```
oCorr(s)=odorCorrect/nTrials;
cCorr(s)=concCorrect/nTrials;
bCorr(s)=bothCorrect/nTrials;
oCorr2(s)=odorCorrect2/nTrials;
cCorr2(s)=concCorrect2/nTrials;
bCorr2(s)=bothCorrect2/nTrials;
oCorr3(s)=odorCorrect3/nTrials;
cCorr3(s)=concCorrect3/nTrials;
bCorr3(s)=bothCorrect3/nTrials;
end % s
save tmp__031805
```

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope and spirit of the invention as set forth. Therefore, many modifications may be made to adapt a particular situation or material to the teachings of the invention without departing from the essential scope and spirit of the present invention. It is intended that the invention not be limited to the particular embodiment disclosed as the best mode contemplated for carrying out this invention, but that the invention will include all embodiments and equivalents falling within the scope of the appended claims.

What is claimed is:

1. A method for identifying molecules comprising:
    flowing at a first flow rate a gaseous matter through a mixing assembly having molecules for mixing the gaseous matter with the molecules to produce a first mixture;
    obtaining a first set of data from the first mixture, wherein obtaining the first set of data from the first mixture comprises sensing the first mixture of gaseous matter and molecules;
    flowing at a second flow rate the gaseous matter through the mixing assembly having the molecules for mixing the gaseous matter with the molecules to produce a second mixture;
    obtaining a second set of data from the second mixture;
    identifying the molecules from the first set of data and from the second set of data; and
    outputting an indication of one or more of the identified molecules.

2. The method of claim 1 additionally comprising controlling the humidity and the temperature of the gaseous matter.

3. The method of claim 1 wherein said identifying the molecules comprises collecting molecular data from the first set of data and from the second set of data, and matching the collected molecular data with known molecular data in order to identify the molecules in the collected molecular data.

4. The method of claim 1 wherein said identifying the molecules comprises controlling a multiplexer assembly to select a sensor, generating a gate voltage waveform, and storing molecular data.

5. The method of claim 1 wherein said identifying the particle comprises collecting particulate data from the matter flowing at the first flow rate and the second flow rate, and matching the collected particulate data with known particulate data in order to identify the particles in the collectd particulate data.

6. The method of claim 1 wherein said obtaining a second set of data from the second mixture comprises sensing the second mixture of gaseous matter and molecules.

7. The method of claim 1 wherein said identifying the molecules comprises combining the first set of date with the second set of date to produce combined molecular data.

8. The method of claim 1 additionally comprising
    flowing at a third flow rate the gaseous matter through the mixing assembly having the molecules for mixing the gaseous matter with the molecules to produce a third mixture;
    obtaining a third set of data;
    identifying the molecules from the first set of data, from the second set of data, and from the third set of data; and
    outputting an indication of one or more of the molecules identified from the first set of data, from the second set of data, and from the third set of data.

9. The method of claim 1 additionally comprising creating in a storage device a database for the molecules prior to producing the first mixture.

10. The method of claim 9 wherein said identifying the molecules comprises identifying the molecules from the first set of data, from the second set of data, and from the database.

11. The method of claim 1 additionally comprising identifying an odor from the identified molecules.

12. A method for identifying a substance comprising:
    flowing through a first mixing assembly and at a first flow rate matter having at least one particle indicative of a substance;
    flowing through a second mixing assembly and at a second flow rate the matter having the at least one particle indicative of the substance;
    obtaining a first set of data from the matter flowing at the first rate, wherein obtaining the first set of data comprises sensing the matter having at least one particle indicative of the substance from the first mixing assembly;
    obtaining a second set of data from the matter flowing at the second rate, wherein obtaining the second set of data from the second mixing assembly comprises sensing the matter having as least one particle indicative of the substance from the second mixing assembly;
    identifying the particle from the first set of data and the second set of data;
    identifying the substance from the identified particle; and
    outputting an indication of the identified substance.

13. The method of claim 12 additionally comprising controlling the humidity and the temperature of the matter.

14. The method of claim 12 wherein said first mixing assembly and said second mixing assembly are the same mixing assembly.

15. The method of claim 12 wherein said first mixing assembly and said second mixing assembly are different mixing assemblies.

16. The method of claim 12 additionally comprising determining the odor of the identified substance from the identified particle.

17. An apparatus for identifying molecules comprising:
 a processing system including a computer;
 a computer-readable medium including instructions executable by the computer comprising
 one or more instructions for setting a first flow rate for a first mixture comprising a gaseous matter and molecules which are to be identified;
 one or more instructions for obtaining a first set of data from the first mixture, wherein the one or more instruction for obtaining the first set of data from the first mixture comprise one or more instruction for sensing the first mixture of gaseous matter and molecules;
 one or more instructions for setting a second flow rate for a second mixture comprising the gaseous matter having the molecules which are to be identified;
 one or more instructions for obtaining a second set of data from the second mixture; and
 one or more instructions for identifying the molecules from the first set of data and from the second set of data.

18. The apparatus of claim 17 wherein said computer-readable medium additionally comprises one or more instructions for controlling the temperature of the gaseous matter; and one or more instructions for controlling the humidity of the gaseous matter.

19. A method for identifying a substance comprising:
 providing an unknown substance which is to be identified;
 flowing through a first mixing assembly and at a first flow rate the unknown substance for obtaining a first set of data;
 flowing through a second mixing assembly and at a second flow rate the unknown substance for obtaining a second set of data;
 obtaining information on the first set of data and on the second set of data, wherein obtaining information on the first set of data comprises sensing the substance flowed through from the first mixing assembly and wherein obtaining information on the second set of data comprises sensing the substance flowed through from the second mixing assembly;
 identifying with an identifying assembly the substance from the information obtained from the first set of data and from the second set of data; and
 outputting an indication of the identified substance.

20. A computer-readable storage medium including instructions executable by a computer, the computer-readable storage medium comprising:
 one or more instructions for setting a first flow rate through a mixing assembly a first mixture comprising gaseous matter and molecules which are to be identified;
 one or more instructions for setting a second flow rate through the mixing assembly a second mixture comprising the gaseous matter and the molecules which are to be identified;
 one or more instructions for identifying the molecules from a first set of data obtained from the first mixture and from a second set of data obtained from the second mixture, wherein obtaining the first set of data from the first mixture comprises one or more instruction for sensing the first mixture of gaseous mater and molecules and wherein obtaining the second set of data from the second mixture comprises one or more instruction sensing the second mixture of gaseous matter and molecules; and
 one or more instructions for outputting an indication of one or more of the identified molecules.

21. The computer readable storage medium of claim 20 additionally comprising:
 one or more instructions for controlling the temperature of the gaseous matter; and
 one or more instructions for controlling the humidity of the gaseous matter.

* * * * *